United States Patent
Cashman et al.

(10) Patent No.: US 10,570,088 B2
(45) Date of Patent: Feb. 25, 2020

(54) BLOOD BRAIN BARRIER-PENETRATING OXIMES FOR CHOLINESTERASE REACTIVATION

(71) Applicant: Human BioMolecular Research Foundation, San Diego, CA (US)

(72) Inventors: John R. Cashman, San Diego, CA (US); Jaroslaw Kalisiak, San Diego, CA (US)

(*) Notice: Subject to any disclaimer, the term of this patent is extended or adjusted under 35 U.S.C. 154(b) by 0 days.

(21) Appl. No.: 15/683,739

(22) Filed: Aug. 22, 2017

(65) Prior Publication Data

US 2017/0349538 A1 Dec. 7, 2017

Related U.S. Application Data

(62) Division of application No. 13/994,682, filed as application No. PCT/US2011/065655 on Dec. 16, 2011, now Pat. No. 9,751,831.

(60) Provisional application No. 61/459,612, filed on Dec. 16, 2010.

(51) Int. Cl.

| | |
|---|---|
| *C07C 251/40* | (2006.01) |
| *C07C 279/12* | (2006.01) |
| *C07C 257/12* | (2006.01) |
| *C07C 257/14* | (2006.01) |
| *C07C 257/18* | (2006.01) |
| *C07D 239/06* | (2006.01) |
| *C07D 249/04* | (2006.01) |
| *C07D 233/24* | (2006.01) |

(52) U.S. Cl.
CPC .......... *C07C 251/40* (2013.01); *C07C 257/12* (2013.01); *C07C 257/14* (2013.01); *C07C 257/18* (2013.01); *C07C 279/12* (2013.01); *C07D 233/24* (2013.01); *C07D 239/06* (2013.01); *C07D 249/04* (2013.01)

(58) Field of Classification Search
CPC .. C07D 251/40; C07D 239/06; C07D 279/12; C07D 257/12; C07D 257/18; C07D 257/14; C07D 249/04; C07D 233/24
See application file for complete search history.

(56) References Cited

PUBLICATIONS

J. Kalisiak et al., Amidine-Oximes:Reactivators for Organophosphate Exposure; Journal of Medicinal Chemistry, 54; pp. 3319-3330, 2011.*

Worek "Recent advances in evaluation of oxime efficiency in nerve agent poisoning by in vitro analysis" Toxicol. Appl. Pharmacol. (2007) 219: 226-234.

* cited by examiner

*Primary Examiner* — Alexander R Pagano
*Assistant Examiner* — Ebenezer O Sackey

(57) ABSTRACT

The invention describes pharmaceutical agents capable of crossing the blood brain barrier to protect against organophosphate pesticides and nerve agents or other electrophiles by reactivating inhibited cholinesterase (i.e., acetylcholinesterase and butyrylcholinesterase) and other proteins in the peripheral and central nervous system.

14 Claims, No Drawings

BLOOD BRAIN BARRIER-PENETRATING OXIMES FOR CHOLINESTERASE REACTIVATION

RELATED APPLICATIONS

The present application is a divisional of pending U.S. patent Ser. No. 13/994,682, filed on Oct. 25, 2013, which is a national phase application from International Application Ser. No. PCT/US2011/065655, filed Dec. 16, 2011, now expired, which claims priority to U.S. Provisional App. No. 61/459,612, filed Dec. 16, 2010, now abandoned, the entire disclosures of which are incorporated by reference herein.

FIELD OF THE INVENTION

The present invention is in the field of pharmaceutical agents and provides compounds and methods for protection from the toxicity of organophosphate and carbamate pesticides, and nerve agents and other covalent inhibitors of biomolecules including enzymes and proteins by using blood brain barrier-penetrating oximes.

BACKGROUND

Organophosphate (OP) and carbamate pesticides and nerve agents and other agents are a significant threat to military personnel and civilians. In addition, farmers, agricultural workers and pesticide applicators handle large amounts of OPs and other agents and are exposed to these toxic materials. Between 150,000 and 300,000 OP-related human toxic incidences are reported annually in the United States (*Lancet*, 338: 223-227, 1991). Additionally, toxic organic compounds are present in industrial materials including jet fuel and other fuel and cause toxicity.

Some examples of toxic agents are that undergo metabolic oxidation to form active organophosphate, "Oxon".

OP and carbamate pesticides and chemical warfare nerve agents and other electrophilic agents are potent covalent inhibitors of proteins and receptors including serine hydrolases including acetylcholinesterase (AChE) and butyrylcholinesterase (BuChE) in the blood and in the central nervous system (CNS). In addition, these agents covalently modify other protetins. Examples of organophosphates include Sarin, Cyclosarin, Soman, Tabun, VX, Diazinon, DFP (2-(Fluoro-(1-methylethoxy)phosphoryl)oxypropane), Fenthion, Malathion, Parathion, Chlorpyrifos, and Echothiophate. Some examples of carbamates include Physostigmine, Neostigmine, Rivastigmine, Methiocarb, and Carbofuran.

Once covalently inhibited, the resulting OP- or carbamate-ChE adduct undergoes slow spontaneous hydrolysis and does not allow ChE to conduct its normal function to hydrolyze the neurotransmitter acetylcholine (ACh). Accordingly, ACh builds up in the synapse and stimulates autonomic receptors and blocks neuromuscular junction receptors. The symptoms resulting from toxic agent exposure are primarily the consequence of accumulation of excess ACh where ordinarily only small amounts of ACh are present at nerve junctions.

Currently, clinically available treatments for acute OP or carbamate poisoning include combined administration of a ChE reactivator (an oxime), a muscarinic receptor antagonist (atropine), and an anticonvulsant (diazepam). Oximes are antidotes for the poisoning and a clinically used drug is available (e.g., 2-PAM (Pralidoxime) containing an oxime group attached to a pyridinium quaternary center.

SUMMARY OF THE INVENTION

Described compounds represent novel classes of structures combining amidine or guanidine and oxime functionalities.

In one embodiment, the present invention provides compounds having pharmacological activity as treatments for organophosphate pesticides and nerve agent or other intoxication agent.

In a typical embodiment, the compounds of the present invention are used to treat toxic effects of organophosphate pesticides and nerve agents or other electrophilic agents.

In another embodiment of the invention, the compounds reactivate pesticide, nerve agent or other electrophilic agent-inhibited human acetylcholinesterase.

In another embodiment of the invention, the compounds reactivate pesticide, nerve agent or other electrophilic agent-inhibited human butyrylcholiesterase.

In another embodiment of the invention, the compounds reactivate carbamate inhibited human acetylcholinesterase.

In another embodiment of the invention, the compounds reactivate carbamate inhibited human butyrylcholiesterase.

In another embodiment of the invention, the compounds penetrate the blood-brain barrier.

In another embodiment, the compounds of the invention are used to increase survival rate upon exposure to organophosphate pesticide, nerve agent or other electrophilic agents.

In another embodiment, the compounds of the invention are used to increase survival rate upon exposure to carbamate pesticide, nerve agent or other electrophilic agents.

In one embodiment of the invention, the compounds are oxime derivatives of the following Formulas I-VII:

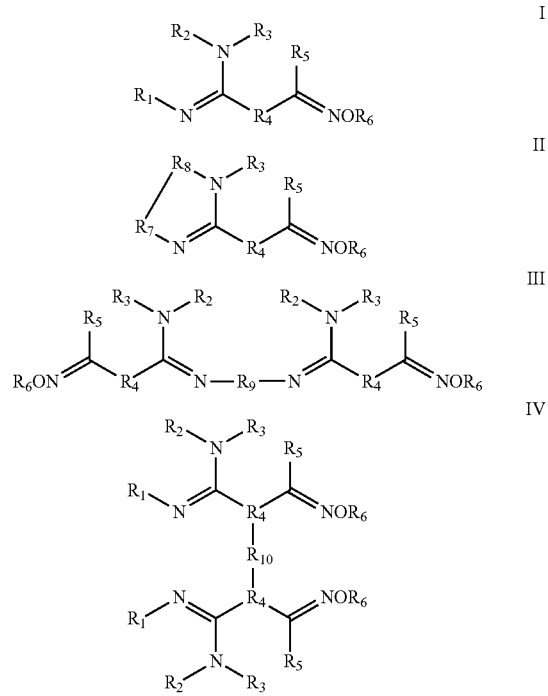

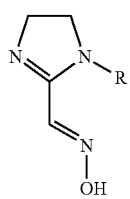

V

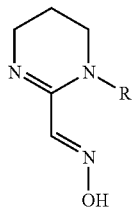

VI

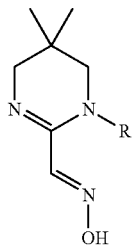

VII where R and $R_1$-$R_{10}$ are as described below.

DETAILED DESCRIPTION

Herein, we report the design of a class of blood-brain-barrier (BBB)-penetrating oximes that combine two important requirements for an effective ChE reactivator: 1) a strongly basic group such as amidine or guanidine to bind to ChE and provide affinity to the target enzyme and 2) a nucleophilic entity such as an oxime functionality capable of removing the adducted ChE by nucleophilic attack and returning ChE to its native state. The BBB-penetrating oximes described herein do not contain a permanent positive charge and can very efficiently enter the CNS and achieve sufficient brain concentrations. It is possible that this is done utilizing a BBB transporter system (i.e., basic amino acid or other cation transporters) because of the similarity of the BBB-penetrating oximes to amino acids although passive diffusion of the BBB-penetrating oxime may be sufficient to achieve the desired concentration in the brain. Once in the brain, the oxime reactivates the inhibited ChE in brain and regenerates functional ChE.

In one embodiment the BBB-penetrating oxime compounds of the present invention are useful in a variety of detoxication applications of organophosphate and carbamate pesticides, nerve agent and other electrophilic and non-electrophilic toxins within and outside the CNS. The present invention further provides pharmaceutical compositions and methods for the treatment of organophosphate and carbamate pesticide, nerve agent and other electrophilic agent exposure. The compounds in the present invention can be delivered or administered to a mammal (e.g., human subject) either alone in the form of a pharmaceutically acceptable salt or hydrolysable precursor thereof or in the form of a pharmaceutical composition wherein the compound is mixed with suitable carriers or excipients in a therapeutically effective amount.

Unless defined otherwise, all technical and scientific terms used herein have the same meaning as commonly understood by one of ordinary skill in the art to which this invention belongs. Although any methods and material similar to those described herein can be used in the practice or testing of the present invention, only exemplary methods and materials are described. For purposes of the present invention, the following terms are defined below.

One diastereomer or enantiomer or geometrical isomers of a compound disclosed herein may display superior biological activity compared with the other. When required, separation of the diastereomers or enantiomers or geometrical isomers can be achieved by formation of a chiral salt and separation by recrystallization, or chromatographic methods. Alternatively, the diastereomers or enantiomers or geometrical isomers may be separated by chromatography using a chiral stationary phase. While not specifying the chirality or geometrical isomerism of the molecule, the technology is applicable to centers of chirality with either stereochemistry. The invention therefore includes all enantiomers, diastereomers, or geometrical isomers or pure forms thereof.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. Suitable indicated groups include, (e.g., alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$, and/or $COOR_y$ wherein each $R_x$ and $R_y$ are independently H, alkyl, alkenyl, aryl, heteroaryl, heterocycle, cycloalkyl or hydroxyl). When a substituent is keto (i.e., =O) or thioxo (i.e., =S) group, then 2 hydrogens on the atom are replaced.

"Alkyl" refers to a $C_1$-$C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$). An alkyl can optionally be substituted with one or more alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$, and/or $COOR_y$ wherein each $R_x$ and $R_y$ are independently H, alkyl, alkenyl, aryl, heteroaryl, heterocycle, cycloalkyl or hydroxyl. The alkyl can optionally be interrupted with one or more non-peroxide oxy (—O—), thio (—S—), carbonyl (—C(=O)—), carboxy (—C(=O)O—), sulfonyl (SO) or sulfoxide (SO2). Additionally, the alkyl can optionally be at least partially unsaturated, thereby providing an alkenyl.

"Alkenyl" refers to a $C_2$-$C_{18}$ hydrocarbon containing normal, secondary, tertiary or cyclic carbon atoms with at least one site of unsaturation, i.e., a carbon-carbon, $sp^2$ double bond. Examples include, but are not limited to: ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$). An alkenyl can optionally be substituted with one or more alkyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and/or $COOR_y$, wherein each $R_x$ and $R_y$ are independently H, alkyl, alkenyl, aryl, heteroaryl, heterocycle, cycloalkyl or hydroxyl. Additionally, the alkenyl can optionally be interrupted with one or more peroxide oxy (—O—), thio (—S—), carbonyl (—C(=O)—), carboxy (—C(=O)O—), sulfonyl ($SO_2$) or sulfoxide (SO).

"Alkylidenyl" refers to a $C_1$-$C_{18}$ hydrocarbon containing normal, secondary, tertiary or cyclic carbon atoms. Examples are methylidenyl (=$CH_2$), ethylidenyl (=$CHCH_3$), 1-propylidenyl (=$CHCH_2CH_3$), 2-propylidenyl (=$C(CH_3)_2$), 1-butylidenyl (=$CHCH_2CH_2CH_3$), 2-methyl-1-propylidenyl (=$CHCH(CH_3)_2$), 2-butylidenyl (=$C(CH_3)CH_2CH_3$), 1-pentylidenyl (=$CHCH_2CH_2CH_2CH_3$), 2-pentylidenyl (=$C(CH_3)CH_2CH_2CH_3$), 3-pentylidenyl (=$C(CH_2CH_3)_2$), 3-methyl-2-butylidenyl (=$C(CH_3)CH(CH_3)_2$), 3-methyl-1-butylidenyl (=$CHCH_2CH(CH_3)_2$), 2-methyl-1-butylidenyl (=$CHCH(CH_3)CH_2CH_3$), 1-hexylidenyl (=$CHCH_2CH_2CH_2CH_2CH_3$), 2-hexylidenyl (=$C(CH_3)CH_2CH_2CH_2CH_3$), 3-hexylidenyl (=$C(CH_2CH_3)(CH_2CH_2CH_3)$), 3-methyl-2-pentylidenyl (=$C(CH_3)CH(CH_3)CH_2CH_3$), 4-methyl-2-pentylidenyl (=$C(CH_3)CH_2CH(CH_3)_2$), 2-methyl-3-pentylidenyl (=$C(CH_2CH_3)CH(CH_3)_2$), and 3,3-dimethyl-2-butylidenyl (=$C(CH_3)C(CH_3)_3$). An alkylidenyl can optionally be substituted with one or more alkyl, alkenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and/or $COOR_y$, wherein each $R_x$ and $R_y$ are independently H, alkyl, alkenyl, aryl, heteroaryl, heterocycle, cycloalkyl or hydroxyl. Additionally, the alkylidenyl can optionally be interrupted with one or more non-peroxide oxy (—O—), thio (—S—), carbonyl (—C(=O)—), carboxy (—C(=O)O—), sulfonyl ($SO_2$) or sulfoxide (SO).

"Alkenylidenyl" refers to a $C_2$-$C_2$ hydrocarbon containing normal, secondary, tertiary or cyclic carbon atoms with at least one site of unsaturation, i.e., a carbon-carbon, $sp^2$ double bond. Examples include, but are not limited to: allylidenyl (=CHCH=$CH_2$), and 5-hexenylidenyl (=$CHCH_2CH_2CH_2$CH=$CH_2$). An alkenylidenyl can optionally be substituted with one or more alkyl, alkenyl, alkylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and/or $COOR_y$, wherein each $R_x$ and $R_y$ are independently H, alkyl, alkenyl, aryl, heteroaryl, heterocycle, cycloalkyl or hydroxyl. Additionally, the alkenylidenyl can optionally be interrupted with one or more non-peroxide oxy (—O—), thio (—S—), carbonyl (—C(=O)—), carboxy (—C(=O)O—), sulfonyl ($SO_2$) or sulfoxide (SO).

"Alkylene" refers to a saturated, branched or straight chain or cyclic hydrocarbon radical of 1-18 carbon atoms, and having two monovalent radical centers derived by the removal of two hydrogen atoms from the same or different carbon atoms of a parent alkane. Typical alkylene radicals include, but are not limited to: methylene (—$CH_2$—), 1,2-ethyl (—$CH_2CH_2$—), 1,3-propyl (—$CH_2CH_2CH_2$—), 1,4-butyl (—$CH_2CH_2CH_2CH_2$—), and the like. An alkylene can optionally be substituted with one or more alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxy alkyl, keto, thioxo, alkylthio, alkylsulfinyl, alkylsulfonyl, cyano, $NR_xR_y$ and/or $COOR_y$, wherein each $R_x$ and $R_y$ are independently H, alkyl, alkenyl, aryl, heteroaryl, heterocycle, cycloalkyl or hydroxyl. Additionally, the alkylene can optionally be interrupted with one or more non-peroxide oxy (—O—), thio (—S—), carbonyl (—C(=O)—), carboxy (—C(=O)O—), sulfonyl ($SO_2$) or sulfoxide (SO). Moreover, the alkylene can optionally be at least partially unsaturated, thereby providing an alkenylene.

A term "alkynyl" refers to unsaturated groups which contain at least one carbon-carbon triple bond and includes straight chain, branched chain, and cyclic groups, all of which may be optionally substituted. Suitable alkynyl groups include ethynyl, propynyl, butynyl and the like which may be optionally substituted.

The term "alkoxy" refers to the group's alkyl-O—, where alkyl is defined herein. Preferred alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like. An alkoxy can optionally be substituted with one or more alkyl, alkylidenyl, alkenylidenyl, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and $COOR_y$, wherein each $R_x$ and $R_y$ are independently H, alkyl, aryl, heteroaryl, heterocycle, cycloalkyl or hydroxyl.

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like. An aryl can optionally be substituted with one or more alkyl, alkenyl, alkoxy, halo, haloalkyl, hydroxy, hydroxyalkyl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$ and $COOR_y$, wherein each $R_x$ and $R_y$ are independently H, alkyl, aryl, heteroaryl, heterocycle, cycloalkyl or hydroxyl.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like. A cycloalkyl can optionally be substituted with one or more alkyl, alkenyl, alkoxy, halo, haloalkyl, hydroxy, hydroxyalkyl, aryl, heteroaryl, heterocycle, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$, and $COOR_y$, wherein each $R_x$ and $R_y$ are independently H, alkyl, aryl, heteroaryl, heterocycle, cycloalkyl or hydroxyl. A cycloalkyl can optionally be at least partially unsaturated, thereby providing a cycloalkenyl.

The term "halo" refers to fluoro, chloro, bromo, and iodo. Similarly, the term "halogen" refers to fluorine, chlorine, bromine, and iodine.

"Haloalkyl" refers to alkyl as defined herein substituted by 1-4 halo groups as defined herein, which may be the same or different. Representative Haloalkyl groups include, by way of example, trifluoromethyl, 3-fluorododecyl, 12,12,12-trifluorododecyl, 2-bromooctyl, 3-bromo-6-chloroheptyl, and the like.

The term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include, but are not limited to, 2H-pyrrolyl, 3H-indolyl, 4Hquinolizinyl, 4nH-carbazolyl, acridinyl, benzo[b]thienyl, benzothiazolyl, β-carbolinyl, carbazolyl, chromenyl, cinnaolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group non-peroxide oxygen, sulfur, and N(Z) wherein Z is absent or is H, O, alkyl, phenyl or benzyl. In another embodiment heteroaryl denotes an ortho-bicyclic heterocycle of about eight to ten ring atoms derived therefrom, particularly a benz-derivative or one derived by fusing a propylene, or tetramethylene diradical thereto. A heteroaryl can optionally be substituted with one or more alkyl, alkenyl, alkoxy, halo, haloalkyl, hydroxy, hydroxyalkyl, aryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$, and $COOR_y$, wherein each $R_x$ and $R_y$ are independently H, alkyl, aryl, heteroaryl, heterocycle, cycloalkyl or hydroxyl.

The term "heterocycle" refers to a saturated or partially unsaturated ring system, containing at least one heteroatom selected from the group oxygen, nitrogen, and sulfur, and optionally substituted with alkyl or $C(=O)OR_b$, wherein $R_b$ is hydrogen or alkyl. Typically heterocycle is a monocyclic, bicyclic, or tricyclic group containing one or more heteroatoms selected from the group oxygen, nitrogen, and sulfur. A heterocycle group also can contain an oxo group (=O) attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine. A heterocycle can optionally be substituted with one or more alkyl, alkenyl, alkoxy, halo, haloalkyl, hydroxy, hydroxyalkyl, aryl, heteroaryl, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$, and $COOR_y$, wherein each $R_x$ and $R_y$ are independently H, alkyl, aryl, heteroaryl, heterocycle, cycloalkyl or hydroxyl. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles. In one specific embodiment of the invention, the nitrogen heterocycle can be 3-methyl-5,6-dihydro-4H-pyrazino[3,2,1-jk]carbazol-3-ium iodide. Another class of heterocycle is known as "crown compounds" which refers to a specific class of heterocyclic compounds having one or more repeating units of the formula [—(CH$_2$-)$_a$A-] where a is equal to or greater than 2, and A at each separate occurrence can be O, N, S or P. Examples of crown compounds include, by way of example only, [—(CH$_2$)$_3$—NH-]$_3$, [4(CH$_2$)$_2$—O)$_4$—((CH$_2$)$_2$—NH)$_2$] and the like. Typically such crown compounds can have from 4 to 10 heteroatoms and 8 to 40 carbon atoms.

The term "alkoxycarbonyl" refers to C(=O)OR, wherein R is an alkyl group as previously defined. The term "alkylamino" refers to —NR$_2$, wherein at least one R is alkyl and the second R is alkyl or hydrogen. The term "acylamino" refers to RC(=O)N, wherein R is alkyl alkylidenyl, aryl, heteroaryl and the like. The term "alkylimino" refers to —C=N—R, wherein R is alkyl alkylidenyl, aryl, heteroaryl and the like. The term "azidoalkyl" refers to —R—N$_3$, wherein R is alkyl, alkylidenyl, aryl, heteroaryl and the like. The term "trifluoromethylalkyl" refers to —R—CF$_3$, wherein R is alkyl alkylidenyl, aryl, heteroaryl and the like. The term "trifluoromethoxyalkyl" refers to R—OCF$_3$, wherein R is alkyl alkylidenyl, aryl, heteroaryl and the like. The term "hydroxy" or "hydroxyl" refers to —OH.

The term "amidinoalkyl" refers to RE(=NR$_1$)NR$_2$R$_3$, wherein R$_1$, R$_2$, R$_3$ is each independently hydrogen, alkyl alkylidenyl, aryl, heteroaryl and the like, and wherein R$_1$, R$_2$, R$_3$ can optionally be substituted with one or more alkyl, alkenyl, alkoxy, oxime, halo, haloalkyl, hydroxy, hydroxy alkyl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$, and $COOR_y$, wherein each $R_x$ and $R_y$ are independently H, alkyl, aryl, heteroaryl, heterocycle, cycloalkyl or hydroxyl.

The term "guanidynoalkyl" refers to $(R_1R_2N)(R_3R_4N)C=N-R_5$, wherein $R_1$, $R_2$, $R_3$, $R_4$ can be an alkyl alkylidenyl, aryl, heteroaryl and the like. The guanidinealkyl, $(R_1R_2N)(R_3R_4N)C=N-R_5$ wherein $R_1$, $R_2$, $R_3$, $R_4$, $R_5$ can optionally be substituted with one or more alkyl, alkenyl, alkoxy, oxime, halo, haloalkyl, hydroxy, hydroxyalkyl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$, and $COOR_y$, wherein each $R_x$ and $R_y$ are independently H, alkyl, aryl, heteroaryl, heterocycle, cycloalkyl or hydroxyl.

The term "oximoalkyl" refers to R-oxime, wherein R is alkyl alkylidenyl, aryl, heteroaryl and the like. An oximoalkyl, R-oxime wherein R can optionally be substituted with one or more alkyl, alkenyl, alkoxy, amidine, guanidine, halo, haloalkyl, hydroxy, hydroxyalkyl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_y$, and $COOR_y$, wherein each $R_x$ and $R_y$ are independently H, alkyl, aryl, heteroaryl, heterocycle, cycloalkyl or hydroxyl.

As used herein, the term "salt" refers to a complex formed between a charged molecule and a suitable counterion to form a neutral species. Example of salts for positively charged compounds include but are not limited to fluoride, chloride, bromide, iodide, acetate, sulfate, nitrate, citrate, oxalate, bicarbonate and the like.

The term "protecting group" refers to a chemical functionality designed to temporarily block a portion of a molecule from chemical modification during synthetic steps. An extensive list of such protecting groups can be found in "Protective Groups in Organic Synthesis", 4th Edition, 2006, by Theodora W. Greene & Peter G. M. Wuts.

The term "prodrug" refers to a chemical group that is attached to compounds of Formula I-VII that undergo removal by a chemical or metabolic or spontaneous process to liberate the parent compound of Formula I-VII. An example would be modification of the oxime oxygen atom with a chemical group (e.g., benzyl or the like) that is chemically or metabolically removed to afford the parent amidine oxime. Such prodrugs might possess advantageous pharmacokinetic or physiochemical properties to aid in drug absorption or distribution.

In one embodiment, disclosed are compounds of the following Formulas I-IV:

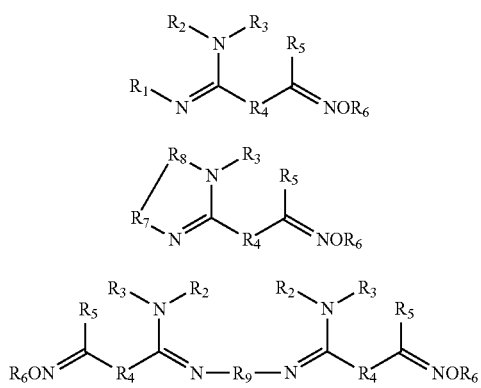

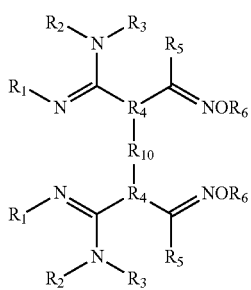

or a pharmaceutically acceptable salt thereof, where

R, $R_1$, $R_2$, and $R_3$ is each independently selected from the group consisting of hydrogen, alkyl, alkenyl, alkynyl, alkylidenyl, alkenylidenyl, alkoxy, halo, haloalkyl, azidoalkyl, hydroxy, hydroxyalkyl, aryl, heteroaryl, heterocycle, cycloalkyl, alkoxycarbonyl, alkylimino, alkylamino, acylamino, trifluoromethylalkyl, trifluoromethoxyalkyl, carboxyalkyl, ketoalkyl, thioalkyl, alkylsulfinyl, alkylsulfonyl, amidinoalkyl, guanidynoalkyl, oximoalkyl, $NR_xR_y$ and/or $COOR_y$ wherein each $R_x$ and $R_y$ are independently hydrogen, alkyl, alkenyl, aryl, heteroaryl, heterocycle, cycloalkyl or hydroxy;

$R_4$ is selected from the group consisting of bond, oxygen, sulfur, nitrogen, alkylene, alkenyl, alkynyl, alkylidenyl, alkenylidenyl, haloalkyl, hydroxyalkyl, aryl, heteroaryl, heterocycle, cycloalkyl, alkoxycarbonyl, alkylimino, alkylamino, acylamino, trifluoromethylalkyl, trifluoromethoxyalkyl, carboxyalkyl, ketoalkyl, thioalkyl, alkylsulfinyl, alkylsulfonyl, amidinoalkyl, guanidynoalkyl, oximoalkyl, $NR_xR_y$ and/or $COOR_y$ wherein each $R_x$ and $R_y$ are independently hydrogen, alkyl, alkenyl, aryl, heteroaryl, heterocycle, cycloalkyl or hydroxy;

$R_5$ is selected from the group consisting of hydrogen, alkyl, alkenyl, alkynyl, alkylidenyl, alkenylidenyl, alkoxy, halo, haloalkyl, azidoalkyl, hydroxy, hydroxyalkyl, aryl, heteroaryl, heterocycle, cycloalkyl, alkoxycarbonyl, alkylimino, alkylamino, acylamino, trifluoromethylalkyl, trifluoromethoxyalkyl, carboxyalkyl, ketoalkyl, thioalkyl, alkylsulfinyl, alkylsulfonyl, amidinoalkyl, guanidynoalkyl, oximoalkyl, $NR_xR_y$ and/or $COOR_y$ wherein each $R_x$ and $R_y$ are independently hydrogen, alkyl, alkenyl, aryl, heteroaryl, heterocycle, cycloalkyl or hydroxy;

$R_6$ is selected from the group consisting of hydrogen, any oxime protecting or masking group that can be removed in physiological or similar conditions to release unprotected oxime (e.g., Methoxymethyl ether (MOM), Methylthiomethyl ether (MTM), Benzyloxymethyl ether (BOM), Benzyl ether (Bn), t-Butoxymethyl ether, Tetrahydropyranyl ether (THP), Tetrahydrothiopyranyl ether, Tetrahydrofuranyl ether, 1-Ethoxyethyl ether (EE), Trimethylsilyl ether (TMS), t-Butyldimethylsilyl ether (TBDMS), Allyl ether, p-Methoxyphenyl ether, p-Methoxybenzyl ether (PMB), Acetate ester (Ac), Trifluoroacetate ester, Benzoate ester (Bz), Pivaloate ester, Methoxymethyl carbonate, Allyl carbonate, 9-Fluorenylmethyl carbonate (Fmoc), Benzyl carbonate);

$R_7$ is selected from the group consisting of oxygen, sulfur, alkylene, alkenyl, alkynyl, alkylidenyl, alkenylidenyl, alkoxy, aryl, heteroaryl, heterocycle, cycloalkyl, carboxyalkyl, ketoalkyl, thioalkyl, alkylsulfinyl, alkylsulfonyl, $NR_xR_y$ and/or $COOR_y$ wherein each $R_x$ and $R_y$ are independently H, alkyl, alkenyl, aryl, heteroaryl, heterocycle, cycloalkyl or hydroxy;

$R_8$ is selected from the group consisting of oxygen, sulfur, alkylene, alkenyl, alkynyl, alkylidenyl, alkenylidenyl, alkoxy, aryl, heteroaryl, heterocycle, cycloalkyl, carboxyalkyl, ketoalkyl, thioalkyl, alkylsulfinyl, alkylsulfonyl, $NR_xR_y$, and/or $COOR_y$, wherein each $R_x$ and $R_y$ are independently hydrogen, alkyl, alkenyl, aryl, heteroaryl, heterocycle, cycloalkyl or hydroxy; and $R_9$ and $R_{10}$ is each independently selected from the group consisting of a bond, oxygen, sulfur, nitrogen, alkylene, alkenyl, alkynyl, alkylidenyl, alkenylidenyl, alkoxy, aryl, heteroaryl, heterocycle, cycloalkyl, carboxyalkyl, ketoalkyl, thioalkyl, alkylsulfinyl, alkylsulfonyl, $NR_xR_y$, and/or $COOR_y$, wherein each $R_x$ and $R_y$ are independently H, alkyl, alkenyl, aryl, heteroaryl, heterocycle, cycloalkyl or hydroxy.

In another embodiment, disclosed are compounds of the following Formulas V-VII.

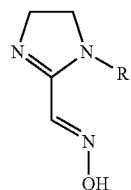

V

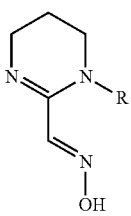

VI

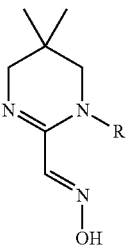

VII or a pharmaceutically acceptable salt thereof, where R is selected from the group consisting of hydrogen, alkyl, alkenyl, alkynyl, alkylidenyl, alkenylidenyl, alkoxy, halo, haloalkyl, azidoalkyl, hydroxy, hydroxyalkyl, aryl, heteroaryl, heterocycle, cycloalkyl, alkoxycarbonyl, alkylimino, alkylamino, acylamino, trifluoromethylalkyl, trifluoromethoxyalkyl, carboxyalkyl, ketoalkyl, thioalkyl, alkylsulfinyl, alkylsulfonyl, amidinoalkyl, guanidynoalkyl, oximoalkyl, $NR_xR_y$, and/or $COOR_y$, wherein each $R_x$ and $R_y$ are independently hydrogen, alkyl, alkenyl, aryl, heteroaryl, heterocycle, cycloalkyl or hydroxy.

The compounds provided herein can be synthesized using known synthetic organic chemistry techniques. Standard synthetic pathways that are used in synthesizing some of the compounds disclosed herein. Those skilled in the art will recognize that these examples are meant to illustrate and not limit the present disclosure.

Additional synthetic procedures are described in the Examples section below.

The methods of use described herein reflect the invention that certain blood-brain barrier-penetrating compounds provide superior and unexpected efficacy in reactivation of butyrylcholinesterase and acetylcholiesterase to decrease mortality in animals exposed to organophosphate nerve agents, pesticides and other toxins.

The present invention further provides pharmaceutical compositions and methods for the treatment of OP poisoning and other CNS-related disorders. Compounds of the present invention can be delivered or administered to a mammal, (e.g., human subject), alone, in the form of a pharmaceutically acceptable salt or hydrolysable precursor or prodrug thereof, or in the form of a pharmaceutical composition wherein the compound is mixed with suitable carriers or excipient(s) in a therapeutically effective amount.

Suitable formulations for use in the present invention are found in, for example, (*Remington's Pharmaceutical Sciences*, Mack Publishing Company, Philadelphia, Pa., 17th ed. 1985 and, *Science*, 249:1527-1533, 1990). The pharmaceutical compositions described herein can be manufactured in a conventional manner, e.g., mixing, dissolving, granulating, dragee-making, levigating, emulsifying, encapsulating, entrapping, or lyophilizing processes.

A pharmaceutically acceptable salt is a non-toxic acid addition salt, which is generally prepared by treating the compounds of the present invention with a suitable organic or inorganic acid. Representative salts include, e.g., hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, and napsylate.

A pharmaceutically acceptable acid addition salt is a salt that retains the biological effectiveness and properties of the free bases and that is not biologically or otherwise undesirable, formed with inorganic acids such as, e.g., hydrochloric acid, hydrobromic acid, sulfuric acid, nitric acid, phosphoric acid, and the like, and organic acids such as, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid, and the like (e.g., *Design of Prodrugs*, Elsevier Science Publishers, Amsterdam, 1985).

The nerve agent protection agents can be formulated with common excipients, diluents or carriers, and compressed into tablets, or formulated as elixirs or solutions for convenient oral administration. The agents can also be formulated as sustained release dosage forms and the like.

For injection, the nerve agent protection agents of the present invention can be formulated into preparations by dissolving, suspending, or emulsifying them in an aqueous or nonaqueous solvent such as, e.g., vegetable or other similar oils, synthetic aliphatic acid glycerides, esters of higher aliphatic acids, or propylene glycol; and, if desired, with conventional additives such as, e.g., solubilizers, isotonic agents, suspending agents, emulsifying agents, stabilizers, and preservatives. Preferably, for injection, the compounds of the present invention can be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

For oral administration, the nerve agent protection agents can be formulated readily by combining with pharmaceutically acceptable carriers that are well-known in the art. Such carriers enable the compounds to be formulated as tablets, pills, dragees, capsules, emulsions, lipophilic and hydrophilic suspensions, liquids, gels, syrups, slurries, suspensions, and the like, for oral ingestion by a subject to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Particularly suitable excipients include fillers such as, for example, sugars (e.g., lactose, sucrose, mannitol, or sorbitol), cellulose preparations (e.g., maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents can be added, such as the cross-linked polyvinyl pyrrolidone, agar, or alginic acid or a salt thereof such as, e.g., sodium alginate.

The invention will be further described by the following examples, meant to illustrate but not limit the invention.

EXAMPLES

While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention. The following examples are offered to illustrate, but not to limit the claimed invention.

Chemical shifts were reported in ppm (δ) relative to $CDCl_3$ at 7.26 ppm or $d_6$-DMSO at 2.50 ppm, respectively.

Example 1

Synthesis of Amidine-oximes

The chemical synthesis of substituted amidine-oxime derivatives 4a-g was efficiently accomplished and products were used to evaluate protection from OP toxins. Compound 1 was converted to amides 2a-g using alkyl amines in refluxing ethanol or 28% $NH_3$ in $H_2O$ (Scheme 1). Thioamides 3a-g were obtained by combining amides 2a-g with Lawesson's reagent in anhydrous THF at 60° C. The amidine-oximes 4a-g were obtained from thioamides 3a-g in two step procedure of an alkylation with methyl triflate and then reaction with $Me_2NH$ solution in THF.

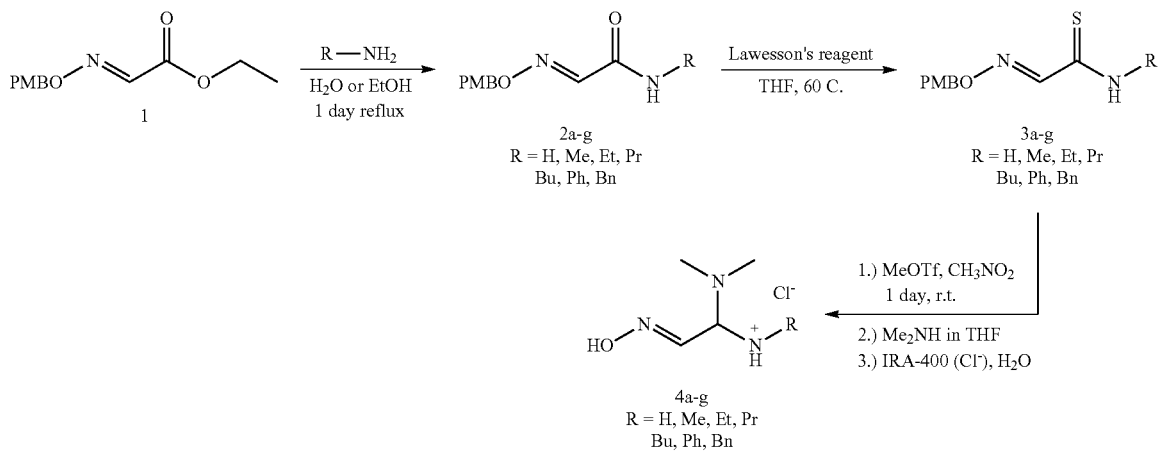

Scheme 1. Synthesis of amidine-oximes 4a-g.

Example 2

Ethyl 2-(4-methoxybenzyloxyimino)-acetate (1)

To NaH (60%, 5.64 g, 141 mmol) in anhydrous DMF (650 mL) at 0-5° C. a solution of ethyl 2-(hydroxyimino)acetate (15 g, 128.2 mmol) in anhydrous DMF (50 mL) was added dropwise, stirred at rt for 1 h and a solution of 1-(chloromethyl)-4-methoxybenzene (17.5 mL, 20.1 g, 128.2 mmol) in anhydrous DMF (50 mL) was added. The reaction was stirred at rt overnight and evaporated. The yellow oil was dissolved in $H_2O$ and $Et_2O$, organic layer was washed with brine, dried over $Na_2SO_4$, filtered, evaporated, purified by chromatography (silica gel, hexanes:EtOAc) to give a light yellow oil (22 g, 72%). $^1$H NMR (300 MHz, $CDCl_3$) δ=7.51 (s, 1H), 7.32 (d, J=8.7 Hz, 2H), 6.90 (d, J=8.7 Hz, 2H), 5.23 (s, 2H), 4.32 (q, J=7.2 Hz, 2H), 3.81 (s, 3H), 1.34 (t, J=7.2 Hz, 3H).

Example 3

2-(4-Methoxybenzyloxyimino)-N-propylacetamide (2d)

A mixture of 1 (4 g, 16.9 mmol) and $PrNH_2$ (2.8 mL, 33.8 mmol) in anhydrous EtOH (50 mL) was stirred at 80° C. overnight, evaporated and purified by chromatography (silica gel, hexanes:EtOAc) to give a yellowish solid (3.75 g, 89%). $^1$H NMR (300 MHz, $CDCl_3$) ϵ=7.43 (s, 1H), 7.29 (d, J=8.4 Hz, 2H), 6.90 (d, J=8.4 Hz, 2H), 6.49 (brs, 1H), 5.11 (s, 2H), 3.81 (s, 3H), 3.28 (q, J=6.9 Hz, 2H), 1.63-1.51 (m, 2H), 0.94 (t, J=7.5 Hz, 3H).

Example 4

2-(4-Methoxybenzyloxyimino)-N-propylethanethioamide (3d)

2d (3.5 g, 14 mmol) and Lawesson's reagent (3.4 g, 8.4 mmol) in anhydrous THF (50 mL) was stirred at 60° C. for 1 h. The mixture was evaporated and purified by chromatography (silica gel, hexanes:EtOAc) to give a yellow oil (3 g 80%). $^1$H NMR (300 MHz, CDCl$_3$) δ=8.19 (brs, 1H), 7.78 (s, 1H), 7.31-7.27 (m, 2H), 6.93-6.88 (m, 2H), 5.12 (s, 2H), 3.82 (s, 3H), 3.69-3.62 (m, 2H), 1.79-1.67 (m, 2H), 1.00 (t, J=7.5 Hz, 3H).

Example 5

2-(Hydroxyimino)-N,N-dimethyl-N'-propylacetimidamide hydrochloride (4d)

To 3d (2.8 g, 10.5 mmol) in MeNO$_2$ (20 mL) at rt, methyl triflate (1.2 mL, 1.7 g, 10.5 mmol) was added. Reaction mixture was stirred at rt overnight and evaporated. The residue was dissolved in anhydrous THF and Me$_2$NH (21 mmol) was added. Reaction was carried out at rt for 30 min., evaporated and the mixture was purified by chromatography (silica gel, CH$_2$Cl$_2$:MeOH) to give 4d. The chloride salt was obtained using IRA-400 (Cl$^-$) ion exchange resin (yellow oil, 880 mg, 43% over 2 steps). $^1$H NMR (300 MHz, DMSO) δ=12.93 (brs, 1H), 9.42 (brs, 1H), 8.08 (s, 1H), 3.30-3.20 (m, 2H, the signal overlaps with residual H$_2$O), 3.15 (s, 6H), 1.59-1.47 (m, 2H), 0.82 (t, J=7.5 Hz, 3H). $^{13}$C NMR (125 MHz, DMSO) δ=157.0, 138.8, 46.3, 41.5, 22.8, 10.7. ESI MS for [M+H]$^+$=157.75 Da.

Example 6

Synthesis of Other Amidine-oximes

Other amidine-oximes were obtained (i.e., 5 and 6 containing azido-alkyl or alkyne substituents, 7a-e with two amidine-oxime moieties linked together through the alkyl or aryl function or 8a-c having a different spacer between the amidine and oxime functions) (Scheme 2).

Scheme 2. Other amidine-oximes.

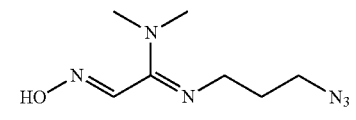

5

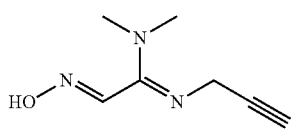

6

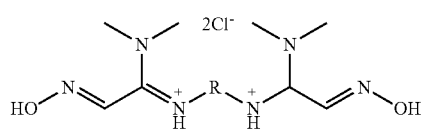

7a R = (CH$_2$)$_2$
7b R = (CH$_2$)$_3$
7c R = (CH$_2$)$_4$
7d R = (CH$_2$)$_5$
7e R = ——(Ph)——

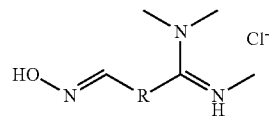

8a R = CH$_2$
8b R = (CH$_2$)$_2$
8c R = (CH$_2$)$_3$

Example 7

Synthesis of Triazole Containing Amidine-oximes

Oximes 5 or 6 can be further modified in the [3+2] cycloaddition reaction with alkynes or azides to form a 1,2,3-triazole heterocycles 9 and 10 (Scheme 3.). Thermal cycloaddition of 5 with 6 afforded the bisfunctional amidine-oxime 11.

Scheme 3. Synthesis of triazole containing amidine-oximes.

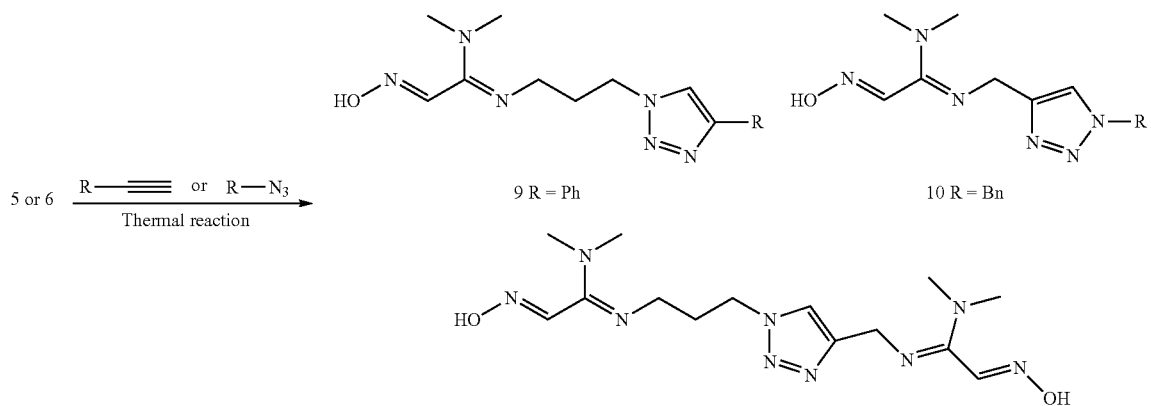

11

Example 8

Synthesis of Aryl-containing Amidine-oximes

Treating 4-formylbenzonitrile 12 in EtOH and $HCl_{gas}$ in $CHCl_3$ gave ethyl 4-formylbenzimidate that was converted to amidines 13a-b with $NH_4Cl$ or $Me_2NH \times HCl$ (Scheme 4).

Amidine-oximes 14a-b were obtained by treating aldehydes 13a-b with 1.1 equiv. of $NH_2OH_{aq}$. Excess of $NH_2OH_{aq}$ (3 equiv.) gave the N-hydroxyamidine 15a-b that is a prodrug form of the amidine-oximes 14a-b with increased bioavailability and BBB permeability. Using similar reaction conditions ortho and meta substituted analogs 15c and bisfunctional amidine-oximes 15d were obtained (Scheme 4.).

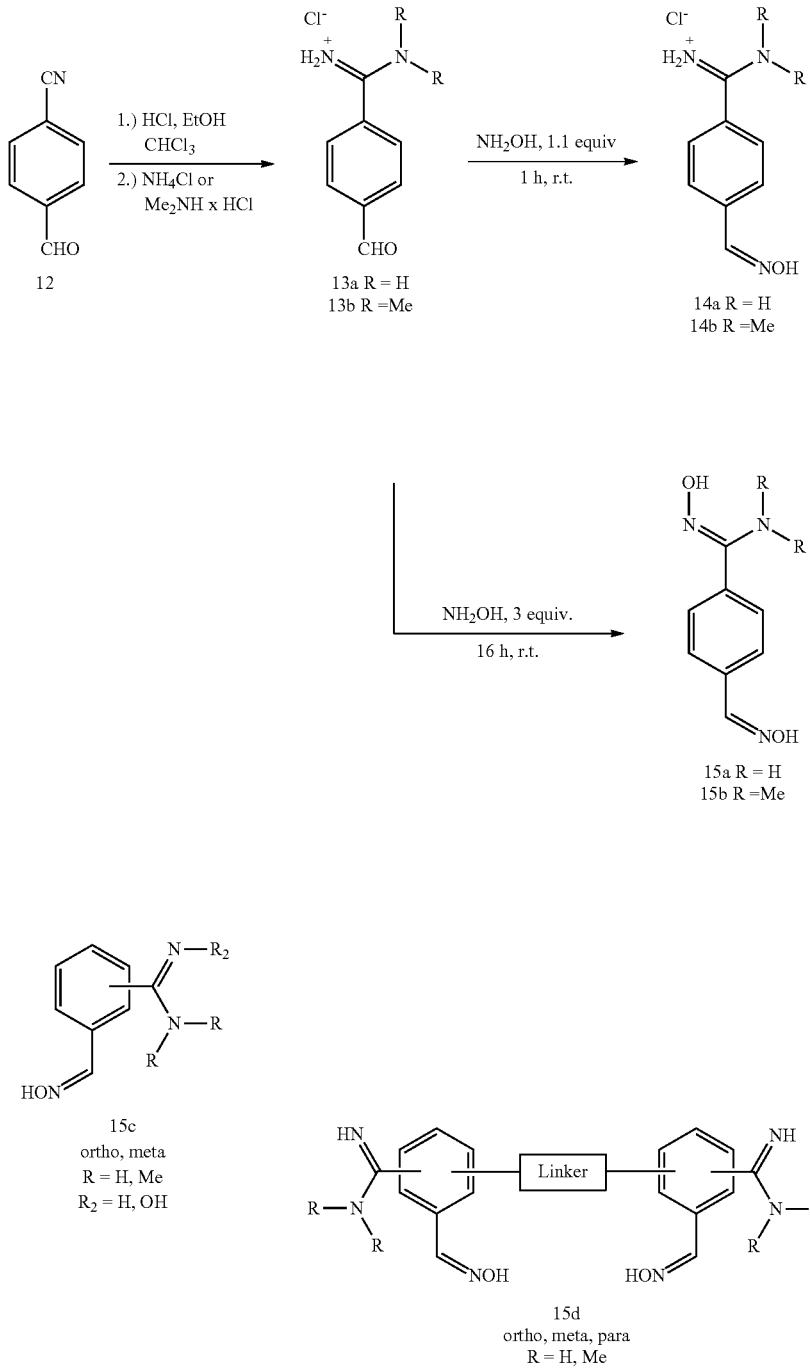

Scheme 4. Synthesis of aryl-containing amidine-oximes.

Example 9

4-Formylbenzamidine hydrochloride (13a)

4-Formylbenzonitrile (10.4 g, 79.4 mmol.), anhydrous EtOH (5.6 mL, 4.4 g, 95.3 mmol) in anhydrous CHCl$_3$ (200 mL) was cooled to 0-5° C. Anhydrous HCl$_{gas}$ was bubbled through the solution for 1 h and kept at 0-5° C. overnight, evaporated, washed with Et$_2$O to give a yellowish solid of ethyl 4-formylbenzimidate hydrochloride (4.8 g, 28%). Ethyl 4-formylbenzimidate hydrochloride (2 g, 9.4 g) was dissolved in H$_2$O (10 mL) and 10% K$_2$CO$_3$ in H$_2$O was added. The mixture was transferred to a separatory funnel, extracted with EtOAc, dried over Na$_2$SO$_4$, filtered and evaporated to give a yellow oil of ethyl 4-formylbenzimidate that was dissolved in MeOH/H$_2$O (9:1, 100 mL) and NH$_4$Cl (550 mg, 10.3 mmol.) was added. The mixture was stirred under reflux for 5 h, evaporated, washed with acetone and purified by chromatography (silica gel, CH$_2$Cl$_2$:MeOH) to give 13a as a white solid (1.2 g, 64%). $^1$H NMR (300 MHz, DMSO) δ=10.12 (s, 1H), 9.42 (brs, 4H), 8.10 (d, J=8.7 Hz, 2H), 7.99 (d, J=8.7 Hz, 2H). ESI MS for [M+H]$^+$=148.95 Da.

Example 10

4-((Hydroxyimino)methyl)benzamidine hydrochloride (14a)

13a (200 mg, 1.1 mmol), 50% NH$_2$OH in H$_2$O (73 µL, 1.2 mmol) in CH$_3$CN:H$_2$O (9:1, 10 mL), stirred at rt for 1 h, evaporated, stirred with anhydrous CH$_3$CN to give a white solid (201 mg, 93%). $^1$H NMR (300 MHz, DMSO) δ=11.70 (s, 1H), 9.44 (brs, 2H), 9.24 (brs, 2H), 8.24 (s, 1H), 7.85 (d, J=8.7 Hz, 2H), 7.78 (d, J=8.7 Hz, 2H). ESI MS for [M+H]$^+$=163.95 Da.

Example 11

N'-Hydroxy-4-((hydroxyimino)methyl)benzamidine (15a)

13a (120 mg, 0.65 mmol), 50% NH$_2$OH in H$_2$O (119 µL, 1.95 mmol) in MeOH was stirred at rt for 16 h, evaporated and purified by chromatography (silica gel, CH$_2$Cl$_2$:MeOH) to give 15a as a yellow solid (90 mg, 77%). $^1$H NMR (300 MHz, DMSO) δ=11.29 (s, 1H), 9.71 (s, 1H), 8.13 (s, 1H), 7.68 (d, J=8.4 Hz, 2H), 7.56 (d, J=8.4 Hz, 2H), 5.82 (brs, 2H). ESI MS for [M+H]±=179.95 Da.

Example 12

Synthesis of Cyclic Amidine-oximes

Oximes 16a and 16b were prepared using previously described literature procedures (*Tetrahedron*, 65:10377-10382, 2009) (Scheme 5).

Scheme 5. Synthesis of aryl-containing amidine-oximes.

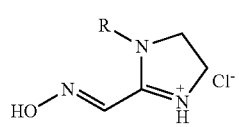

16a

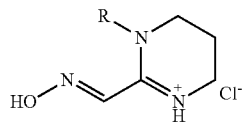

16b

Example 13

1-Benzyl-4,5-dihydro-1H-imidazole-2-carbaldehyde oxime hydrochloride (16a, R=Bn)

$^1$H NMR (300 MHz, DMSO) δ=13.60 (brs, 1H), 10.43 (brs, 1H), 8.42 (s, 1H), 7.48-7.25 (m, 5H), 4.85 (s, 2H), 3.82 (s, 4H). ESI MS for [M+H]±=203.95 Da.

Synthesis of Guanidine-oximes.

A synthetic route to a diverse set of guanidine-oximes is depicted (Scheme 6). Amine-oximes (e.g., 17) can be obtained via standard organic chemistry techniques involving nitro-reduction and/or phthalimide type-amino protection and aldehyde or acetal derived oxime syntheses. From 17 many distinct routes allow access to guanidine-oximes with the desired substitution pattern by using guanylation agents, and protected thiourea (18) as synthetic intermediate.

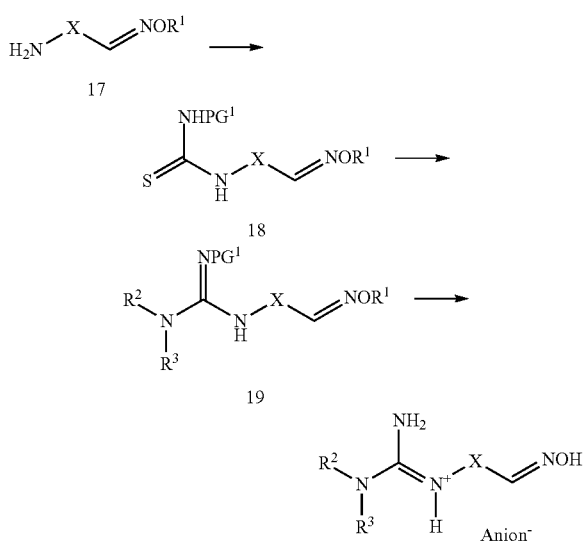

Scheme 6. Synthesis of guanidine-oximes.

X = Alkyl/Aryl linker group; PG = thiourea/guanidine protecting group (e.g. carbamate or sulfonamide type); R$^1$ = H, hydroxy protecting group; R$^2$, R$^3$, R$^4$ = H, Alkyl/Aryl groups.

Example 14

4-Aminobenzaldehyde oxime (17, X=—C$_6$H$_4$—)

$^1$H NMR (300 MHz, DMSO) δ=5.41 (brs, 2H), 6.51 (m, 2H), 7.22 (m, 2H), 7.87 (s, 1H) 10.54 (s, 1H). HPLC/MS (ESI): 137 [M+H]+, 119 [M−H$_2$O+H]+.

Example 15

4-[(N-Benzyloxycarbonyl)thioureido]benzaldehyde oxime (18, X=—C$_6$H$_4$—)

18 mL of a 0.5 M stock solution of benzyloxycarbonyl isothiocyanate (9 mmol) were added dropwise to a solution of 4-aminobenzaldehyde oxime (17) (1.2 g, 8.81 mmol) in 200 mL of anhydrous CH$_2$Cl$_2$ at room temperature while stirring. This solution is stirred for another two hours. Precipitated product was removed by filtration (740 mg of a yellow-orange solid). The organic phase was concentrated to ca. 50 mL, and 50 mL of hexanes were added. Another 700 mg of precipitated product were obtained by filtration. The filtrate was subjected to flash chromatography using hexanes/EtOAc, 20-40% to yield another crop of the desired product. Yield: 1.61 g (55%).

$^1$H NMR (300 MHz, DMSO) δ=5.25 (s, 2H), 7.41 (m, 5H), 7.62 (m, 4H), 8.13 (s, 1H), 11.26 (s, 1H), 11.45 (brs, 1H), 11.55 (brs, 1H).

Example 16

4-[(N-Benzyloxycarbonyl)-N',N'-(dimethyl)-guanidino]benz-aldehyde oxime (19, X=—C$_6$H$_4$—)

400 mg of 4-[(N-benzyloxy-carbonyl)thioureido]benzaldehyde oxime (18) (1.18 mmol), 458 mg DIPEA (3.54 mmol) and 144 mg of dry dimethylamine hydrochloride (1.77 mmol) were dissolved in 25 mL of anhydrous CH$_2$Cl$_2$ and cooled to 0° C. 339 mg of EDCI (1.77 mmol) was added and the mixture was stirred for 24 h at rt until TLC indicated complete consumption of the thiourea 18. The mixture was concentrated and the crude product was purified by flash chromatography on silica gel using CH$_2$Cl$_2$/MeOH (0-5%) followed by a second purification using hexanes/EtOAc (20-40%) as the eluent. Yield: 361 mg (90%). $^1$H NMR (300 MHz, CDCl$_3$) ε=2.91 (s, 6H), 5.14 (s, 2H), 6.96 (brd, J=8.4 Hz, 2H), 7.26-7.43 (m, 6H), 7.51 (brd, J=8.4 Hz, 2H), 8.08 (s, 1H), 10.46 (brs, 1H). HPLC/MS (ESI): 341 [M+H]$^+$, 297 [M-N(CH$_3$)$_2$+H]$^+$.

Example 17

4-[N',N'-(dimethyl)guanidino]benzaldehyde oxime Trifluoro-acetate (20, X=—C$_6$H$_4$—)

170 mg of 4-[(N-benzyloxycarbonyl)-N',N'-(dimethyl)guanidino] benzaldehyde oxime (19) (0.5 mmol) was dissolved in 10 mL TFA and 1.54 mL thioanisole and stirred at room temperature for 6 hours. The mixture was concentrated and purified twice on silica gel by flash chromatography and finally by preparative TLC (CH$_2$Cl$_2$/MeOH, 0-40%) to yield the product as a white crystalline solid. Yield: 80 mg (50%). $^1$H NMR (300 MHz, D$_2$O) δ=3.12 (s, 6H), 7.29 (brd, J=8.4 Hz, 2H), 7.66 (brd, J=8.4 Hz, 2H), 8.24 (s, 1H). HPLC/MS (ESI): 207 [M+H]$^+$.

Example 18

Binding Affinity

Binding affinities of oximes 4a-g to hAChE and hBuChE (i.e., IC$_{50}$ values) were determined by titrating oxime concentrations over a range of 3 to 100 μM using enzymatic assays with 1 mM substrate and fitting the observed rates of turnover to a simple binding isotherm. For example, an oxime 4e inhibits hAChE with an IC$_{50}$ value of 54±8 μM (n=1) and inhibits hBChE with an IC$_{50}$ value estimated larger than 300 μM.

Example 19

Lipophilic Amidine-oximes

Based on the above findings, amidine-oximes containing lipophilic (i.e., propyl and butyl) substituents on the amidine function had the greatest reactivation rate of OP-ChE. Herein we explored the effect of more bulky substituents on the amidine functionality. The PMB-protected ethyl glyoxylate oxime 21 was readily converted to amides 22a-j using aliphatic (a-f), cycloalkyl (g, h) or aromatic (i, j) amines (Table 1). Thioamides 23a-j were obtained in good yield using a standard protocol employing Lawesson's reagent. The final step of the synthesis was an activation of the carbonyl group via S-methylation of thioamides 23a-j. This step was carried out using 1.2 equivalents of MeOTf. Previously, we reported that traces of water in the reaction mixture caused hydrolysis of MeOTf and formed triflic acid in situ and under these acidic conditions the oxime protecting group (i.e., PMB) was efficiently cleaved. Without any purification the crude mixture was used in the synthesis of amidine hydrochlorides 24a-j after treatment with the dimethylamine solution and salt exchange. This synthetic methodology was successfully used to prepare over 10 g of amidine 24b.

TABLE 1

Synthesis of amidine-oximes 24a-j.

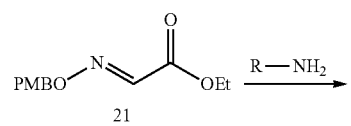

21

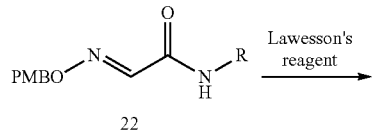

22

TABLE 1-continued

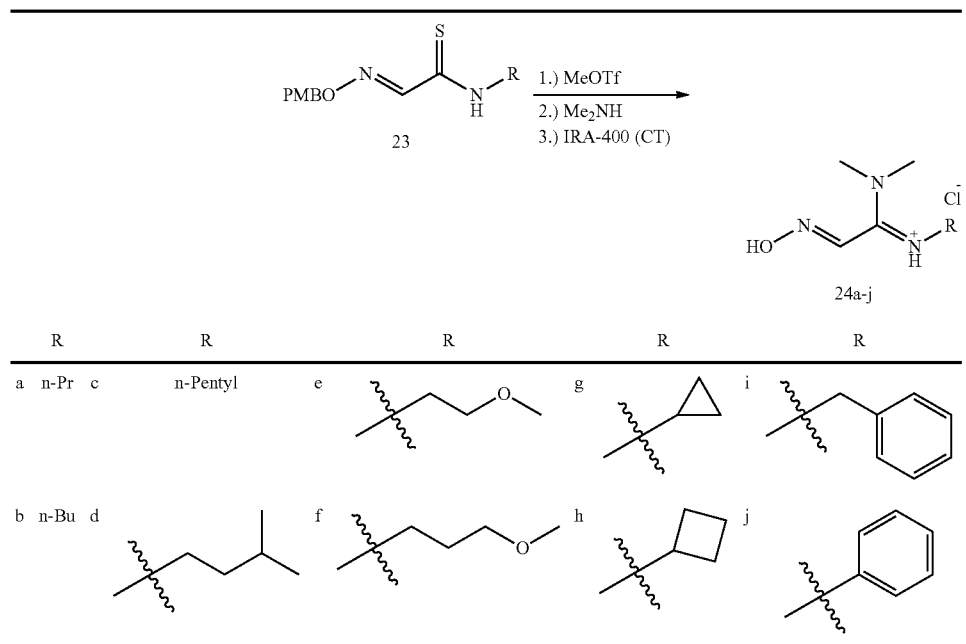

| | R | | R | | R | | R | | R |
|---|---|---|---|---|---|---|---|---|---|
| a | n-Pr | c | n-Pentyl | e | (CH₂CH₂OMe) | g | cyclopropylmethyl | i | benzyl |
| b | n-Bu | d | isohexyl | f | (CH₂CH₂CH₂OMe) | h | cyclobutylmethyl | j | phenyl |

After successful synthesis of oximes 24a-j, we explored the synthesis of cyclic amidine-oxime analogs. The synthesis of cyclic amidine-oximes was accomplished using a method that started with 1,1-bis(methylthio)-2-nitroethylene 25. Subsequent treatment of 25 with the requisite diamine afforded the 5-member (26) or 6-member (27) nitro vinyl intermediate (Table 2). Mono-alkylation of 26 or 27 was accomplished using alkyl iodides (a, e, f) or benzyl chlorides (b, c, d, g-i). The final step of the synthesis of 29a-i was two electron reduction of 28a-i employing $SnCl_2 \times 2H_2O$ (Table 2).

Example 20

Compound 24b is obtained from commercially available starting materials in three steps in acceptable overall yield.

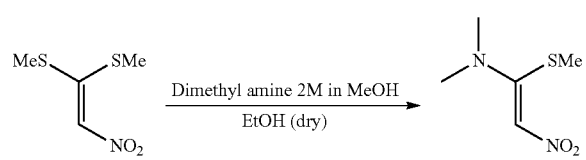

Synthesis of (Z)—N-(1-(methylthio)-2-nitrovinyl)-N,N-dimethyl amine

Commercially available 1,1-bis (methylthio)-2-nitroethylene (200 mg, 1.2 mmol), dimethyl amine (600 μL, 1.2 mmol) and dry THF (12 mL) were mixed in a microwave vial and heated for 3 min at 125° C. After the reaction was judged complete by TLC (1:1 Hex:Acetone) the material was purified by flash chromatography Hex→30% Acetone in Hex to afford 93.7 mg, 48% yield of the target compound. (Rf=0.43 in 1:1 H/A).
$^1$H NMR (500 MHz, CDCl$_3$) δ □2.44 (s, 3H), 3.18 (s, 6H), 6.65 (s, 1H).

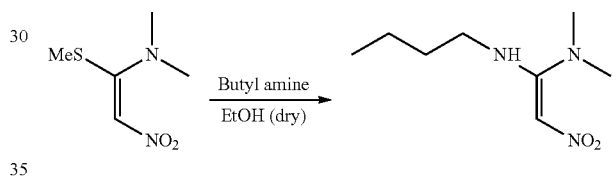

Synthesis of (Z)—N-butyl-N,N-dimethyl-2-nitroethene-1,1-diamine 89.5 mg of the dimethylamino compound 0.55 mmol, dry EtOH (600 μL) and butyl amine (82 μL, 0.83 mmol) were mixed in a microwave vial and heated at 125° C. for 2 h. TLC (1:1 Hex:Acetone) showed product that was purified by flash chromatography Hex→60% Acetone in Hex to afford an orange oil (48 mg, 47% yield). (Rf=0.33 in 1:1 H/A). $^1$H NMR (500 MHz, CDCl$_3$) δ=0.92 (t, J=7.4 Hz, 3H), 1.41 (q, J=7.4 Hz, 2H), 1.64 (sept, J=7.4 Hz, 2H), 2.90 (s, 6H), 3.25 (sext, J=7.4 Hz, 2H), 6.49 (s, 1H), 9.60 (bs, 1H).

Synthesis of N'-butyl-2-(hydroxyimino)-N,N-dimethylacetimidamide (24b)

To the nitroethene (11.2 mg, 0.05 mmol) was added dry DCM (190 μL) and $SnCl_2 \times 2H_2O$ (63 mg, 0.28 mmol), the reaction was stirred at room temperature overnight. NaHCO$_3$ (71.4 mg, 0.85 mmol) with 200 μL dry DCM was added and stirred at RT overnight. The resulting yellow oil 84% yield was identical to 24b after conversion to the HCL salt. $^1$H NMR (300 MHz, DMSO) δ=12.97 (brs, 1H), 9.29 (brs, 1H), 8.07 (s, 1H), 3.15 (s, 6H), 2.93 (s, 3H).

Example 21

2-(Hydroxyimino)-N,N-dimethyl-N'-pentylacetimidamide hydrochloride salt (24c)

To a solution of 23c (3.0 g, 10.2 mmol) in MeNO$_2$ (20 mL) at rt, MeOTf (1.4 mL, 2.0 g, 12.2 mmol, 1.2 equiv) was added. The reaction mixture was stirred at rt for 3 days and then evaporated. The crude product was dissolved in anhydrous THF (100 mL) and Me$_2$NH (2M in THF, 10.2 mL, 20.4 mmol, 2 equiv) was added. The reaction was carried out at rt 1 h and then evaporated. The residue was purified by column chromatography (silica gel, CH$_2$Cl$_2$→9:1, CH$_2$Cl$_2$:MeOH) to give 24c as the triflate salt. The chloride salt was obtained using an IRA-400 (Cl$^-$) ion exchange resin (yellow oil, 1.0 g, 44%). $^1$H NMR (300 MHz, d$_6$-DMSO) δ=12.92 (s, 1H), 9.95 (br s, 1H), 8.08 (s, 1H), 3.31-3.23 (m, 2H), 3.17 (br s, 3H), 3.13 (br s, 3H), 1.56-1.46 (m, 2H), 1.30-1.18 (m, 4H), 0.84 (t, J=6.9 Hz, 3H). $^{13}$C NMR (125 MHz, d$_6$-DMSO) δ=157.0, 138.8, 44.6, 41.0, 33.9, 29.1, 27.9, 21.6, 13.7. ESI MS for [M+H]$^+$=185.9 Da.

Example 22

2-(Hydroxyimino)-N'-isopentyl-N,N-dimethyl-acetimidamide hydrochloride salt (24d)

The title compound was obtained similar to 24c, as a yellow oil (48%). $^1$H NMR (300 MHz, d$_6$-DMSO) δ=12.93 (s, 1H), 9.53 (br s, 1H), 8.09 (s, 1H), 3.33-3.24 (m, 2H), 3.17 (br s, 3H), 3.13 (br s, 3H), 1.58-1.38 (m, 3H), 0.84 (d, J=6.6 Hz, 6H). $^{13}$C NMR (125 MHz, d$_6$-DMSO) δ=157.0, 138.8, 43.0, 41.4, 38.4, 24.9, 22.2. ESI MS for [M+H]$^+$=185.9 Da.

Example 23

2-(Hydroxyimino)-N'-(2-methoxyethyl)-N,N-dimethylacetimidamide hydrochloride salt (24e)

The title compound was obtained similar to 24c, as a yellow oil (53%). $^1$H NMR (300 MHz, d$_6$-DMSO) δ=12.95 (s, 1H), 9.70 (br s, 1H), 8.05 (s, 1H), 3.59-3.36 (m, 4H), 3.25-3.22 (m, 3H), 3.19-3.11 (m, 6H). ESI MS for [M+H]$^+$=173.8 Da.

Example 24

2-(Hydroxyimino)-N'-(3-methoxypropyl)-N,N-dimethylacetimidamide hydrochloride salt (24f)

The title compound was obtained similar to 24c, as a yellow oil (34%). $^1$H NMR (300 MHz, d$_6$-DMSO) δ=12.94 (s, 1H), 9.67 (br s, 1H), 8.05 (s, 1H), 3.39-3.26 (m, 4H), 3.21-3.11 (m, 9H), 1.87-1.72 (m, 2H). ESI MS for [M+H]$^+$=187.9 Da.

Example 25

N'-Cyclopropyl-2-(hydroxyimino)-N,N-dimethyl-acetimidamide hydrochloride salt (24g)

The title compound was obtained similar to 24c, as a yellow solid (22%). $^1$H NMR (300 MHz, d$_6$-DMSO) δ=12.94 (br s, 1H), 9.62 (br s, 1H), 8.10 (s, 1H), 3.16-3.09 (m, 6H), 2.82-2.58 (m, 1H), 0.89-0.70 (m, 4H). $^{13}$C NMR (125 MHz, d$_6$-DMSO) δ=159.2, 139.4, 42.0, 33.9, 26.6, 7.5. ESI MS for [M+H]$^+$=155.9 Da.

Example 26

N'-Cyclobutyl-2-(hydroxyimino)-N,N-dimethyl-acetimidamide hydrochloride salt (24h)

The title compound was obtained similar to 24c, as a yellow oil (23%). $^1$H NMR (500 MHz, d$_6$-DMSO) δ=12.95 (s, 1H), 9.31 (br s, 1H), 8.04 (s, 1H), 4.16-4.07 (m, 1H), 3.25-3.12 (m, 6H), 2.30-2.21 (m, 2H), 2.19-2.12 (m, 2H), 1.68-1.60 (m, 2H). $^{13}$C NMR (125 MHz, d$_6$-DMSO) δ=156.1, 139.0, 50.2, 41.4, 33.9, 29.9, 14.1. ESI MS for [M+H]$^+$=169.9 Da.

Example 27

N'-Benzyl-2-(hydroxyimino)-N,N-dimethylacetimidamide hydrochloride salt (24i)

The title compound was obtained similar to 24c, as a yellow solid (48%). $^1$H NMR (300 MHz, d$_6$-DMSO) δ=10.20 (br s, 1H), 9.18 (br s, 1H), 8.82 (br s, 1H), 7.41-7.29 (m, 5H), 4.47 (s, 2H), 3.21-3.13 (m, 6H). ESI MS for [M+H]$^+$=205.9 Da.

Example 28

2-(Hydroxyimino)-N,N-dimethyl-N'-phenylacetimidamide hydrochloride salt (24j)

The title compound was obtained similar to 24c, as a yellow solid (10%). $^1$H NMR (300 MHz, d$_6$-DMSO) δ=12.85 (br s, 1H), 11.48 (br s, 1H), 7.79 (s, 1H), 7.44-7.38 (m, 2H), 7.31-7.25 (m, 1H), 7.22-7.19 (m, 2H), 3.32 (br s, 6H). $^{13}$C NMR (125 MHz, d$_6$-DMSO) δ=156.4, 139.9, 137.0, 129.2, 126.9, 125.4, 41.7, 33.9. ESI MS for [M+H]$^+$=191.9 Da.

TABLE 2

Synthesis of cyclic amidine-oximes 29a-i.

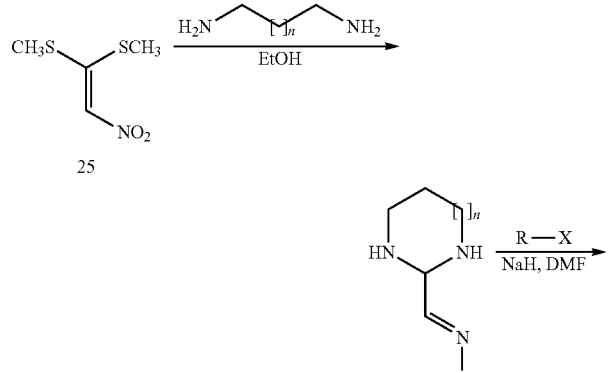

26 n = 0
27 n = 1

TABLE 2-continued

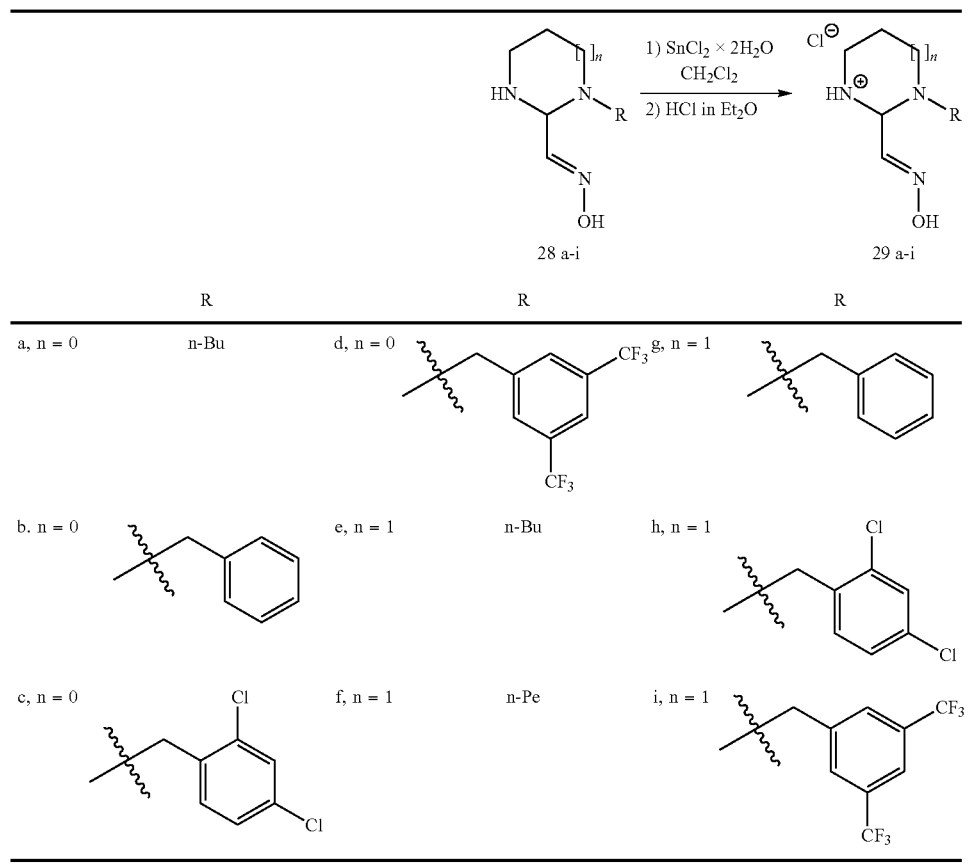

Example 29

1-Butyl-4,5-dihydro-1H-imidazole-2-carbaldehyde oxime hydrochloride (29a)

To a solution of 29a (2.2 g, 11.9 mmol) in anhydrous $CH_2Cl_2$ (100 mL) was added solid $SnCl_2 \times 2\, H_2O$ (14.7 g, 65.4 mmol, 5.5 equiv). The reaction mixture was stirred overnight at rt and then solid $NaHCO_3$ (17.0 g, 202.3 mmol, 17.0 equiv) was carefully added in small portions. After addition the mixture was stirred for 1 day at rt and then diluted with MeOH (100 mL). The suspension was filtered through Celite, washed with MeOH (3×100 mL) and evaporated. The crude product was purified by column chromatography (silica gel, $CH_2Cl_2 \rightarrow 8:2$, $CH_2Cl_2$:MeOH). The isolated product, in the free base form, was dissolved in $CH_2Cl_2$:MeOH (9:1) and an excess of 2M HCl in $Et_2O$ was added and the mixture was evaporated to give a yellow oil (0.46 g, 19%). $^1H$ NMR (300 MHz, $d_6$-DMSO) δ=13.50 (s, 1H), 10.13 (br s, 1H), 8.27 (s, 1H), 4.00-3.76 (m, 4H), 3.56 (t, J=7.2 Hz, 2H), 1.58-1.48 (m, 2H), 1.32-1.19 (m, 2H), 0.88 (t, J=7.2 Hz, 3H). ESI MS for [M+H]+=169.9 Da.

Example 30

1-(2,4-Dichlorobenzyl)-4,5-dihydro-1H-imidazole-2-carbaldehyde oxime hydrochloride (29c)

The title compound was obtained similar to 29a, as a yellow solid (30%). $^1H$ NMR (300 MHz, $d_6$-DMSO) δ=13.59 (s, 1H), 10.65 (br s, 1H), 8.40 (s, 1H), 7.72 (d, J=1.8 Hz, 1H), 7.55-7.47 (m, 2H), 4.93 (s, 2H), 3.88-3.76 (m, 4H). $^{13}C$ NMR (125 MHz, $d_6$-DMSO) δ=159.0, 135.1, 133.8, 133.7, 131.4, 130.8, 129.2, 127.8, 49.6, 47.3, 42.8. ESI MS for [M+H]+=271.9 Da.

Example 31

1-(3,5-bis(Trifluoromethyl)benzyl)-4,5-dihydro-1H-imidazole-2-carbaldehyde oxime hydrochloride (29d)

The title compound was obtained similar to 29a, as a yellow solid (41%). $^1H$ NMR (300 MHz, $d_6$-DMSO) δ=13.53 (s, 1H), 10.58 (br s, 1H), 8.42 (s, 1H), 8.18 (br s, 2H), 8.12 (br s, 1H), 5.00 (s, 2H), 3.82 (br s, 4H). $^{13}C$ NMR (125 MHz, $d_6$-DMSO) δ=159.2, 137.9, 135.4, 130.5 (q, J=32.9 Hz), 129.2, 123.2 (q, J=271.2 Hz), 121.9, 49.7, 48.8, 42.8. ESI MS for [M+H]+=340.0 Da.

Example 32

1-Butyl-1,4,5,6-tetrahydropyrimidine-2-carbaldehyde oxime hydrochloride (29e)

The title compound was obtained similar to 29a, as a pink solid (28%). $^1H$ NMR (300 MHz, $d_6$-DMSO) δ=13.06 (s, 1H), 9.69 (br s, 1H), 8.27 (s, 1H), 3.56-3.48 (m, 4H), 3.30-3.36 (m, 2H), 1.96-1.88 (m, 2H), 1.58-1.48 (m, 2H), 1.31-1.19 (m, 2H), 0.87 (t, J=7.2 Hz, 3H). $^{13}C$ NMR (125 MHz, $d_6$-DMSO) δ=153.0, 138.5, 51.3, 46.3, 38.1, 29.6, 18.9, 18.3, 13.5. ESI MS for [M+H]+=184.1 Da.

Example 33

1-Pentyl-1,4,5,6-tetrahydropyrimidine-2-carbaldehyde oxime hydrochloride (29f)

The title compound was obtained similar to 29a, as a brown oil (42%). $^1$H NMR (500 MHz, d$_6$-DMSO) δ=13.20 (s, 1H), 9.90 (br s, 1H), 8.27 (s, 1H), 3.55-3.50 (m, 4H), 3.35-3.30 (m, 2H), 1.96-1.90 (m, 2H), 1.59-1.53 (m, 2H), 1.31-1.17 (m, 4H), 0.86 (t, J=7.2 Hz, 3H). $^{13}$C NMR (125 MHz, d$_6$-DMSO) δ=152.9, 138.4, 51.5, 46.3, 38.1, 27.7, 27.2, 21.7, 18.3, 13.7. ESI MS for [M+H]$^+$=198.0 Da.

Example 34

1-(2,4-Dichlorobenzyl)-1,4,5,6-tetrahydropyrimidine-2-carbaldehyde oxime hydrochloride (29h)

The title compound was obtained similar to 29a, as a yellow solid (21%). $^1$H NMR (300 MHz, d$_6$-DMSO) δ=13.10 (s, 1H), 10.19 (br s, 1H), 8.26 (s, 1H), 7.72 (d, J=2.1 Hz, 1H), 7.52-7.40 (m, 2H), 4.90 (s, 2H), 3.48-3.35 (m, 4H), 2.02-1.92 (m, 2H). $^{13}$C NMR (125 MHz, d$_6$-DMSO) δ=154.2, 138.8, 133.5, 133.3, 131.1, 130.4, 129.2, 127.8, 52.5, 46.6, 38.3, 18.1. ESI MS for [M+H]$^+$=285.9 Da.

Example 35

1-(3,5-Bis(trifluoromethyl)benzyl)-1,4,5,6-tetrahydropyrimidine-2-carbaldehyde oxime hydrochloride (29i)

The title compound was obtained similar to 29a, as a yellow solid (63%). $^1$H NMR (300 MHz, d$_6$-DMSO) δ=13.05 (s, 1H), 10.11 (br s, 1H), 8.35 (s, 1H), 8.11-8.06 (m, 3H), 5.02 (s, 2H), 3.49-3.32 (m, 4H), 1.99-1.85 (m, 2H). $^{13}$C NMR (125 MHz, d$_6$-DMSO) δ=154.3, 139.2, 138.5, 130.6 (q, J=32.9 Hz), 128.8, 123.2 (q, J=271.3 Hz), 121.8, 53.7, 46.5, 38.3, 18.1. ESI MS for [M+H]$^+$=354.0 Da.

Additional analogs 32a,b containing two geminal methyl groups in the 6-member ring structure were synthesized to examine whether an increase in lipophilicity improved the overall pharmaceutical properties of reactivators (Scheme 7).

Scheme 7. Synthesis of cyclic amidine-oximes 32a,b.

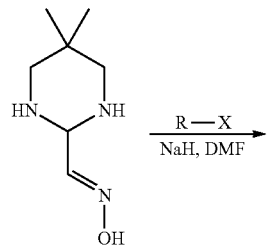

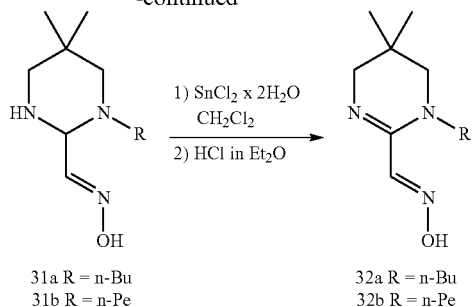

31a R = n-Bu
31b R = n-Pe

32a R = n-Bu
32b R = n-Pe

Example 36

1-Butyl-5,5-dimethyl-1,4,5,6-tetrahydropyrimidine-2-carbaldehyde oxime hydrochloride (32a)

The title compound was obtained similar to 29a, as a yellow solid (37%). $^1$H NMR (500 MHz, d$_6$-DMSO) δ=13.22 (br s, 1H), 9.98 (br s, 1H), 8.29 (s, 1H), 3.54-3.51 (m, 2H), 3.29 (br s, 2H), 3.06 (br s, 2H), 1.57-1.51 (m, 2H), 1.31-1.22 (m, 2H), 0.97 (s, 6H), 0.88 (t, J=7.2 Hz, 3H). $^{13}$C NMR (125 MHz, d$_6$-DMSO) δ=152.3, 138.2, 56.7, 51.2, 48.9, 29.6, 25.9, 23.1, 18.9, 13.5. ESI MS for [M+H]$^+$=212.1 Da.

Example 37

5,5-Dimethyl-1-pentyl-1,4,5,6-tetrahydropyrimidine-2-carbaldehyde oxime hydrochloride (32b)

The title compound was obtained similar to 29a, as a yellow solid (35%). $^1$H NMR (500 MHz, d$_6$-DMSO) δ=13.22 (br s, 1H), 9.98 (br s, 1H), 8.29 (s, 1H), 3.54-3.50 (m, 2H), 3.27 (br s, 2H), 3.06 (br s, 2H), 1.59-1.52 (m, 2H), 1.31-1.20 (m, 4H), 0.98 (s, 6H), 0.86 (t, J=7.2 Hz, 3H). $^{13}$C NMR (125 MHz, d$_6$-DMSO) δ=152.2, 138.2, 56.7, 51.4, 48.9, 27.7, 27.2, 25.9, 23.1, 21.6, 13.7. ESI MS for [M+H]$^+$=226.2 Da.

Example 38

Reactivation Studies

The ability of oximes 4a-g and 16a-b to reactivate ChEs inhibited by nerve agent model compounds was evaluated using an Ellman's assay (*Biochem Pharmacol* 7:88-95, 1961). Amidine-oximes 4a-g and 16a-b were tested for ChE reactivation using 21 and 22, cyclosarin and sarin model compounds (*Chem Res Toxicol* 22:1669-1679, 2009; *Chem Res Toxicol* 22:1680-1688, 2009).

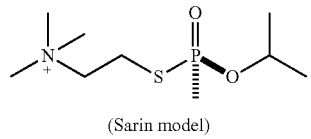

21

(Sarin model)

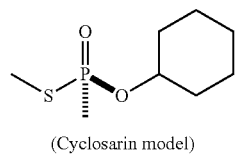

(Cyclosarin model)

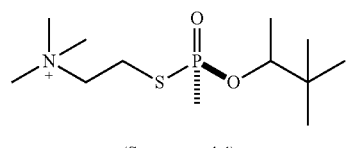

(Soman model)

In a typical assay, hBChE or hAChE was diluted in PBS/BLG (pH=7.4), and a sample was taken and set aside for non-inhibited controls. The remaining portion was incubated with a nerve agent model compound for sufficient time to achieve 90% or greater inhibition (i.e., ca. 15 min). The reaction of the enzyme with nerve agent model compounds afforded covalent modification of the enzyme identical to that obtained with authentic nerve agents. An excess of OP was removed from inhibited enzyme by filtration through a 10 kDa MWCO filter with a modified PES membrane, followed by two washes prior to the final resuspension in PBS/BLG (pH=7.4). An excess of 1000-fold dilution of OP was achieved. Enzyme was then added to PBS/BLG (pH=7.4) containing amidine-oxime, MINA or 2-PAM (100 μM oxime with 2% DMSO after addition of enzyme) or vehicle. Enzyme was allowed to reactivate at room temperature for 20 min (hBuChE) or 1 h (hAChE), at which time the catalytic activity was determined using a modified Ellman's assay in the presence of 1 mM substrate in PBS/BLG (pH=7.4). Assay concentrations were used in the range of 10 to 50 units $L^{-1}$, where 1 unit cleaves 1 μmole of substrate per min in PBS pH 7.4, room temperature. Two reactivation samples were prepared per oxime. The reported data show the average esterase activity for each oxime divided by the average activity of non-inhibited control samples, and the propagated errors of the average activities. Based on the results (Table3) uncharged oximes 4a-g and 16a-b are superior reactivators compared to MINA (i.e., an uncharged oxime) and are comparable for reactivation as the clinically used drug 2-PAM (Table3).

TABLE 3

Reactivation of 21 and 22 inhibited hAChE and hBuChE:

| Oxime[a] | Reactivation of 21-inhibited ChEs[b], Relative activity [%] | | Reactivation of 22-inhibited ChEs[b], Relative activity [%] | |
|---|---|---|---|---|
| | hAChE | hBuChE | hAChE | hBuChE |
| 4a | 31 | 46 | 5 | 55 |
| 4b | 26 | 73 | 8 | 89 |
| 4c | 25 | 89 | 10 | 88 |
| 4d | 23 | 92 | 7 | 89 |
| 4e | 19 | 93 | 7 | 97 |
| 4f | 9 | 79 | 3 | 73 |
| 4g | 6 | 47 | 2 | 78 |
| 16a | 29 | 61 | 32 | 90 |
| 16b | 29 | 73 | 8 | 77 |
| 2-PAM | 74 | 65 | 23 | 60 |
| MINA | 4 | 4 | 4 | 17 |
| No oximes | 1 | 3 | 1 | 6 |

[a]All compounds were hydrochloride salts.

[b]Relative enzymatic activity after 20 min. incubation to sample not treated with 21 or 22.

TABLE 4

Mean ± standard deviation for the relative reactivation of OP-inhibited hAChE and hBChE by amidine-oximes 24a-j. Results for reactivation of ETP- and Sp-GA-inhibited ChE were identical and presented in the same column. Top-3 results for each OP-ChE reactivation experiment have been highlighted.

| | AChE | | | BChE | | |
|---|---|---|---|---|---|---|
| Oxime | Sp-GB | Sp-GF | Sp-GA/ETP | Sp-GB | Sp-GF | Sp-GA/ETP |
| 2-PAM | 0.88 ± 0.04 | 0.41 ± 0.04 | 0.60 ± 0.13 | 0.65 ± 0.01 | 0.57 ± 0.06 | 0.23 ± 0.05 |
| MINA | 0.12 ± 0 | 0.12 ± 0 | 0.14 ± 0.01 | 0.04 ± 0 | 0.17 ± 0.01 | 0.02 ± 0 |
| 24a | 0.51 ± 0.05 | 0.09 ± 0.01 | 0.34 ± 0.03 | 0.98 ± 0.05 | 1.02 ± 0.11 | 0.26 ± 0 |
| 24b | 0.44 ± 0.04 | 0.20 ± 0.01 | 0.34 ± 0.05 | 0.93 ± 0.07 | 0.97 ± 0.04 | 0.27 ± 0.01 |
| 24c | 0.42 ± 0.03 | 0.11 ± 0.01 | 0.30 ± 0.01 | 0.84 ± 0.01 | 0.86 ± 0.11 | 0.11 ± 0.04 |
| 24d | 0.49 ± 0.03 | 0.08 ± 0.01 | 0.24 ± 0.01 | 0.55 ± 0.04 | 0.84 ± 0.12 | 0.06 ± 0.01 |
| 24e | 0.20 ± 0.01 | 0.03 ± 0 | 0.08 ± 0.03 | 0.51 ± 0.04 | 0.33 ± 0.01 | 0.07 ± 0.02 |
| 24f | 0.21 ± 0.01 | 0.04 ± 0.01 | 0.08 ± 0.01 | 0.54 ± 0.01 | 0.46 ± 0.02 | 0.06 ± 0.02 |
| 24g | 0.61 ± 0.04 | 0.11 ± 0.01 | 0.15 ± 0.01 | 0.73 ± 0.05 | 0.56 ± 0.03 | 0.13 ± 0.03 |
| 24h | 0.51 ± 0.04 | 0.12 ± 0.01 | 0.17 ± 0.02 | 0.86 ± 0.05 | 0.58 ± 0.04 | 0.14 ± 0.01 |
| 24i | 0.15 ± 0.01 | 0.05 ± 0.01 | 0.11 ± 0.01 | 0.47 ± 0.05 | 0.78 ± 0.03 | 0.04 ± 0 |
| 24j | 0.22 ± 0.01 | 0.07 ± 0.01 | 0.16 ± 0.04 | 0.79 ± 0.04 | 0.73 ± 0.03 | 0.18 ± 0.01 |

TABLE 5

Mean ± standard deviation for the relative reactivation of OP-inhibited hAChE and hBChE by cyclic amidine-oximes 29a-i and 32a, b. Results for reactivation ETP- and Sp-GA-inhibited ChE were identical and presented in the same column. Top-3 results for each OP-ChE reactivation experiment have been highlighted.

| | AChE | | | BChE | | |
|---|---|---|---|---|---|---|
| Oxime | Sp-GB | Sp-GF | Sp-GA/ETP | Sp-GB | Sp-GF | Sp-GA/ETP |
| 2-PAM | 0.88 ± 0.04 | 0.41 ± 0.04 | 0.60 ± 0.13 | 0.65 ± 0.01 | 0.57 ± 0.06 | 0.23 ± 0.05 |
| MINA | 0.12 ± 0 | 0.12 ± 0 | 0.14 ± 0.01 | 0.04 ± 0 | 0.17 ± 0.01 | 0.02 ± 0 |
| 29a | 0.60 ± 0.1 | 0.21 ± 0.02 | 0.29 ± 0.01 | 0.46 ± 0.02 | 0.76 ± 0.08 | 0.08 ± 0.03 |
| 29b | 0.55 ± 0.06 | 0.27 ± 0.01 | 0.43 ± 0.07 | 0.66 ± 0.07 | 0.90 ± 0.01 | 0.14 ± 0 |
| 29c | 0.35 ± 0.08 | 0.33 ± 0.02 | 0.40 ± 0.07 | 0.86 ± 0.01 | 0.66 ± 0.06 | 0.10 ± 0.03 |
| 29d | 0.12 ± 0.01 | 0.12 ± 0.02 | 0.27 ± 0.01 | 0.76 ± 0.01 | 1.15 ± 0.04 | 0.17 ± 0.01 |
| 29e | 0.81 ± 0.15 | 0.16 ± 0 | 0.37 ± 0.06 | 0.88 ± 0.01 | 0.95 ± 0.12 | 0.20 ± 0.04 |
| 29f | 0.39 ± 0.07 | 0.13 ± 0.03 | 0.35 ± 0.05 | 0.66 ± 0.06 | 0.89 ± 0.01 | 0.20 ± 0.04 |
| 29g | 0.55 ± 0.01 | 0.10 ± 0.01 | 0.40 ± 0.05 | 0.77 ± 0.06 | 0.91 ± 0.12 | 0.14 ± 0.01 |
| 29h | 0.26 ± 0.06 | 0.21 ± 0.01 | 0.29 ± 0.06 | 0.86 ± 0.01 | 0.80 ± 0.13 | 0.34 ± 0.07 |
| 29i | 0.22 ± 0.01 | 0.22 ± 0.01 | 0.33 ± 0.01 | 1.02 ± 0.02 | 1.09 ± 0.20 | 0.32 ± 0.03 |
| 32a | 0.51 ± 0.03 | 0.08 ± 0.01 | 0.18 ± 0.01 | 0.86 ± 0.07 | 0.76 ± 0.17 | 0.13 ± 0.04 |
| 32b | 0.34 ± 0.04 | 0.09 ± 0 | 0.24 ± 0.03 | 0.92 ± 0.01 | 0.84 ± 0.1 | 0.16 ± 0.07 |

Example 39

ADMET and Pharmacokinetic Studies

Prior to in vivo PK studies, we conducted chemical and metabolic stability of 24b and backups. Incubation of 24b in the presence of phosphate buffer (pH 7.4) at room temperature or elevated temperature showed that 24b was quite stable. The half life for aqueous degradation was 153 hr at room temperature, 118 hr at 60° C. and 71 hr at 80° C. We conclude 24b is more than sufficiently stable for use in the emergency setting or on the battlefield. In preparation for in vivo studies, we next examined the metabolic stability in hepatic microsomes. Compound 24b was incubated in the presence of rat, mouse and human liver microsomes±NADPH. 24b was quantified after an extractive workup with a validated HPLC method. No significant metabolic instability was observed for 24b in rat liver microsomes. In the presence of mouse or human liver microsomes, the half life was 108 and 90 min, respectively, also indicating metabolic stability. Because lack of metabolism could be due to inhibition of cytochrome P-450 (CYP), we examined the possible inhibition of prominent CYPs by 24b and analogs. 24b did not significantly inhibit CYP. To confirm this, the effect of 24b on the microsomal metabolism of testosterone was examined. No appreciable effect of 24b on testosterone hydroxylase functional activity was observed using a validated HPLC assay.

A separate cohort of animals were dosed with 24b (i.v. and i.m., n=5) and at time of $C_{max}$ were killed and peripheral blood and brains were taken, homogenized, extracted and analyzed by LCMS. For i.v. administration (6 mg/kg) 12.9±1.6 µg/gram of brain:1.9±1 µg/ml plasma gave a brain to plasma ratio of 6.7 to 1. For the i.m. dose (25 mg/kg) 14±2.8 µg/gram of brain:16.7±10 µg/ml plasma gave a brain to plasma ratio of almost 1. The brain to blood ratio for both i.v. and i.m. showed good brain bioavailability. Samples were also analyzed for inhibition of ChE in the brain and plasma. Compared to untreated animals, no significant ChE inhibition of either blood or brain ChE was observed. The conclusion is that significant levels of 24b got into the brain after i.v. or i.m. administration to rats and this is safe and no apparent ChE inhibition is observed. Compound 24b was tested for signs of toxicity in dose escalation studies in mice and rats. In mice, no apparent toxicity was observed up to a dose of 200 mg/kg. In rats, no apparent toxicity was seen until 200 mg/kg was administered. We conclude that this class of compounds is generally non-toxic.

Pharmacokinetic studies were done in male rats and showed that 24b rapidly moved into the brain. The half life was approximately 2 hours. Cmax was 30 mins for both iv and im routes of administration. The relatively rapid entry into the brain is highly desirable for a nerve agent detoxication agent to decrease the toxicity of nerve agents post exposure.

Example 40

In Vivo Studies

Two oximes 4c-d were tested for their efficacy to protect mice against toxicity of nerve agent model compound (23) (Table 3). In this study, separate groups of adult Swiss Webster female mice received amidine-oximes or a positive control compound, 2-PAM. or vehicle pretreated (i.p.) 30 min prior to 23 (0.25 mg/kg, i.p.). Each test compound and 2-PAM as hydrochloride salts were dissolved in isotonic saline and administered to separate groups in a volume of 1 ml/kg. The survival rate was recorded after 24 h from an experiment (Table 3). In an initial experiment, animals were pretreated with vehicle or 4c at a dose of 100 mg/kg (i.p.) to evaluate protection from initial toxicity. For vehicle-treated animals, only 2/14 control animals survived to the 24 h time point whereas all animals pretreated with 4c survived (Table 3). In a second experiment, animals were pretreated with either amidine-oximes 4c-d or 2-PAM at the same molar concentration, (i.e., 145 µmol, 26 mg/kg for 4c, 28 mg/kg for 4d and 25 mg/kg for 2-PAM). In this second experiment, amidine-oximes 4c-d provided complete protection to animals whereas 2-PAM protected only 6/8 mice. In the third experiment, animals were pretreated with only 25% of the previous oxime dose (i.e., 6.5 mg/kg for 4c and 6.25 mg/kg for 2-PAM). In this experiment none of animals from the 2-PAM-treated group survived, whereas 4c protected 4/6 animals.

TABLE 6

In-vivo effect of 4c-d on 23 nerve agent model compound-treatment survival.

| Oxime Pretreatment (mg/kg)[a] | OP Treatment (mg/kg)[c] | Survival (24 hr) |
|---|---|---|
| Vehicle | 0.25 | 2/14 |
| Oxime 4c (100 mg/kg)[b] | | 6/6 |
| Oxime 4c (26 mg/kg)[b] | | 6/6 |
| Oxime 4d (28 mg/kg)[b] | | 6/6 |
| 2-PAM (25 mg/kg) | | 6/8 |
| Oxime 4c (6.5 mg/kg)[b] | | 4/6 |
| 2-PAM (6.25 mg/kg) | | 0/6 |

[a]Mice were pretreated (i.p. injection) with vehicle or oxime 30 min prior to 23 nerve agent model compound.
[b]Compounds 4b-c were hydrochloride salts.
[c]23 nerve agent model compound.

TABLE 7

Effect of vehicle, MINA, 2-PAM or amidine-oximes on lethality of Sp-GB-Am.

| | | Sp-GB-Am | | | |
|---|---|---|---|---|---|
| Experiment | Treatment[a] | μmole/mg | mg/kg | μmole/kg | Survival (24 h) |
| 1 | Vehicle | — | 0.08 | 0.305 | 6/11 |
| | MINA (12.6 mg/kg) | 145 | | | 3/6 |
| | 2-PAM (25.0 mg/kg) | | | | 6/6 |
| | 24a (28.0 mg/kg) | | | | 6/6 |
| | 24b (30.1 mg/kg) | | | | 6/6 |
| | 24c (32.1 mg/kg) | | | | 6/6 |
| | 29a (29.6 mg/kg) | | | | 6/6 |
| | 29b (34.6 mg/kg) | | | | 4/6 |
| | 29c (44.6 mg/kg) | | | | 6/6 |
| | 29d (54.3 mg/kg) | | | | 5/6 |
| | 29e (31.7 mg/kg) | | | | 6/6 |
| | 29f (33.7 mg/kg) | | | | 6/6 |
| | 32a (35.7 mg/kg) | | | | 2/6 |
| | 32b (37.8 mg/kg) | | | | 6/6 |
| 2 | 2-PAM (6.2 mg/kg) | 36.2 | | | 6/6 |
| | 24b (7.5 mg/kg) | | | | 6/6 |
| | 29a (7.4 mg/kg) | | | | 5/6 |
| | 29e (7.9 mg/kg) | | | | 6/6 |

[a]Mice were treated (i.p.) with Sp-GB-Am and 5 min later vehicle or amidine-oxime or MINA or 2-PAM was administered. All oximes were administered as a hydrochloride salt in isotonic saline.

As shown in Table 7, for Sp-GB-Am-pretreatment, post exposure administration of vehicle protected only 6/11 animals for survival to 24 h. Mice experienced significant CNS toxicity including seizures, lack of spontaneous activity and no interest in food consumption. Similar symptoms were observed for the MINA-treated group, that only protected 3/6 animals from lethality. At a dose of 145 μmoles/kg, non-cyclic amidine oximes 24a-c and cyclic amidine oximes 24a, 24c, 24e, and 24f protected all animals challenged with a lethal dose of Sp-GB-Am. After 24 h from OP exposure the amidine oxime treated animals behaved similar to non-OP treated animals and showed no significant symptoms of toxicity. Likewise, after pretreatment of animals with OP, post-administration of amidine-oxime 32b protected all OP-treated mice that survived the treatment and showed behavioral activity comparable with healthy, untreated animals. Next, a lower dose (i.e., 36 μmole/kg) of oxime was shown to protect mice from OP pretreatment. As shown in Table 7, amidine oxime 24b and 24e fully protected from pre-administration of Sp-GB-Am in a dose-dependent fashion comparable to an equimolar dose of 2-PAM.

Protection from a lethal dose of sarin by 24b in guinea pigs. To examine the efficacy of the amidine oximes in a animal model exposed to a real nerve agent, the effect of 24b post-administration was examined. After a 1.5×LD50 of sarin was administered to guinea pigs, administration of 36 mg/kg of 24b protected 100% of the guinea pigs dosed (8/8 animals dosed).

Summary: 4a-d, 24 and 32 hydrochlorides were effective agents for in-vivo protection against nerve agent model compound toxicity and lethality. Compound 24b was effective at protecting against. sarin nerve agent toxicity. The present invention further provides pharmaceutical compositions and methods for the treatment of OP poisoning and other CNS-related disorders. Compounds 4b-c, 24 and 32 of the present invention can be delivered or administered to a mammal, (e.g., human subject), alone, in the form of a pharmaceutically acceptable salt or hydrolysable precursor or prodrug thereof, or in the form of a pharmaceutical composition wherein the compound is mixed with suitable carriers or excipient(s) in a therapeutically effective amount.

What is claimed is:

1. A compound of Formula 1:

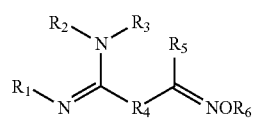

or a pharmaceutically acceptable salt thereof, wherein
$R_1$, $R_2$, and $R_3$ is each independently selected from the group consisting of alkyl, cycloalkyl, alkoxyalkyl, aryl, heteroaryl, arylalkyl and heteroarylalkyl;
$R_4$ is a bond;
$R_5$ is selected from the group consisting of hydrogen and alkyl; and
$R_6$ is selected from the group consisting of hydrogen and an oxime protecting group capable of removal under physiological conditions to release unprotected oxime or $R_6$ is Methoxymethyl ether (MOM), Methylthiomethyl ether (MTM), Benzyloxymethyl ether (BOM), Benzyl ether (Bn), t-Butoxymethyl ether, Tetrahydropyranyl ether (THP), Tetrahydrothiopyranyl ether, Tetrahydrofuranyl ether, 1-Ethoxyethyl ether (EE), Trimethylsilyl ether (TMS), t-Butyldimethylsilyl ether (TBDMS), Allyl ether, p-Methoxyphenyl ether, p-Methoxybenzyl ether (PMB), Acetate ester (Ac), Trifluoroacetate ester, Benzoate ester (Bz), Pivaloate ester, Methoxymethyl carbonate, Allyl carbonate, 9-Fluorenylmethyl carbonate (Fmoc), or Benzyl carbonate,
provided the compound in which $R_6$ is hydrogen or is deprotected to hydrogen is capable of reactivating organophosphate-inhibited human acetylcholinesterase and butyrylcholiesterase.

2. The compound of claim 1, wherein
$R_1$, $R_2$, and $R_3$ is each independently hydrogen or alkyl; and
$R_5$ and $R_6$ are each hydrogen.

3. The compound of claim 2, wherein $R_1$ is selected from the group consisting of methyl, ethyl, n-propyl, i-propyl, n-butyl, i-butyl, s-butyl, and t-butyl.

4. The compound of claim 3, wherein $R_1$ is n-butyl.

5. The compound of claim 2, wherein $R_2$ and $R_3$ is each independently selected from the group consisting of methyl, ethyl, n-propyl, i-propyl, n-butyl, i-butyl, s-butyl, and t-butyl.

6. The compound of claim 5, wherein $R_2$ and $R_3$ is each independently methyl.

7. The compound of claim 1, wherein the compound is an amidine-oxime of Table 1.

8. The compound of claim 1, wherein the compound is 2-(Hydroxyimino)-N,N-dimethyl-N'-butylacetimidamide.

9. A pharmaceutical composition comprising a compound of claim 1 and a pharmaceutically acceptable excipient or carrier.

10. The pharmaceutical composition of claim 9, wherein the compound is an amidine-oxime of Table 1.

11. The pharmaceutical composition of claim 9, wherein the compound is 2-(Hydroxyimino)-N,N-dimethyl-N'-butylacetimidamide.

12. A method of treating nerve agent poisoning in a subject, the method comprising: administering to the subject in need thereof an effective amount of a compound of claim 1.

13. The method of claim 12, wherein the compound is an amidine-oxime of Table 1.

14. The method of claim 12, wherein the compound is 2-(Hydroxyimino)-N,N-dimethyl-N'-butylacetimidamide.

* * * * *